United States Patent [19]
Howard, III

[11] Patent Number: 5,843,093
[45] Date of Patent: Dec. 1, 1998

[54] STEREOTACTIC ELECTRODE ASSEMBLY

[75] Inventor: Matthew A. Howard, III, Iowa City, Iowa

[73] Assignee: University of Iowa Research Foundation, Iowa City, Iowa

[21] Appl. No.: 549,165

[22] Filed: Oct. 27, 1995

Related U.S. Application Data

[63] Continuation-in-part of Ser. No. 194,017, Feb. 9, 1994, Pat. No. 5,469,369, which is a continuation-in-part of Ser. No. 332,755, Nov. 11, 1994.

[51] Int. Cl.$^6$ .................................................. A61B 19/00
[52] U.S. Cl. ..................... 606/130; 606/185; 607/116; 600/372; 600/373; 600/377; 600/378
[58] Field of Search .................................. 607/116, 115, 607/2, 53, 54, 48, 75, 62; 128/642, 644, 635; 606/130, 213, 215, 129, 185, 48, 50; 604/167, 165, 164, 264; 623/10, 25; 600/372, 373, 374, 377, 378, 379

[56] References Cited

U.S. PATENT DOCUMENTS

| | | | |
|---|---|---|---|
| 3,147,750 | 9/1964 | Fry | 128/642 |
| 4,461,304 | 7/1984 | Kuperstein | 128/642 |
| 4,762,135 | 8/1988 | Van Der Puije et al. | 607/116 |
| 4,892,102 | 1/1990 | Astrinsky | 128/642 |
| 4,907,589 | 3/1990 | Cosman | 606/34 |
| 5,000,194 | 3/1991 | Van Den Honert et al. | 623/10 |
| 5,119,832 | 6/1992 | Xavier | 128/642 |
| 5,176,652 | 1/1993 | Littrell | 604/167 |
| 5,341,807 | 8/1994 | Nardella | 606/38 |
| 5,380,288 | 1/1995 | Hart et al. | 606/185 |
| 5,385,146 | 1/1995 | Goldreyer | 606/33 |
| 5,385,560 | 1/1995 | Wulf | 604/260 |
| 5,405,375 | 4/1995 | Ayers et al. | 128/642 |
| 5,429,131 | 7/1995 | Scheinman et al. | 128/642 |
| 5,462,544 | 10/1995 | Saksena et al. | 128/642 |
| 5,531,759 | 7/1996 | Kensey et al. | 606/215 |
| 5,545,193 | 8/1996 | Fleischman et al. | 607/116 |
| 5,545,200 | 8/1996 | West et al. | 128/642 |
| 5,545,201 | 8/1996 | Helland et al. | 128/642 |
| 5,545,219 | 8/1996 | Kuzma | 623/10 |
| 5,582,609 | 12/1996 | Swanson et al. | 128/642 |
| 5,584,847 | 12/1996 | Duluco et al. | 606/185 |

*Primary Examiner*—Linda C. Dvorak
*Attorney, Agent, or Firm*—Fleshner & Kim

[57] ABSTRACT

A neural prosthetic device for an auditory cortex of a patient has a support arranged in the auditory cortex with a plurality of electrical contacts and is connected to a speech processor for receiving and processing audio information and outputting processed electrical signals. Each of the plurality of electrical contacts independently outputs electrical discharges in accordance with the processed electrical signals. The plurality of electrical contacts are arranged to approximately tonotopically match the auditory cortex.

And, methods and apparatus for selectively treating or inactivating neurons within the brain of a patient. The apparatus includes a dual purpose multicontact neuron-monitoring electrode assembly and an introducer tube for introducing the electrode assembly within a patient in the vicinity of the target tissue. The apparatus and methods of the instant invention are particularly suited to performing magnetic pallidotomy for the treatment of Parkinson's disease.

21 Claims, 29 Drawing Sheets

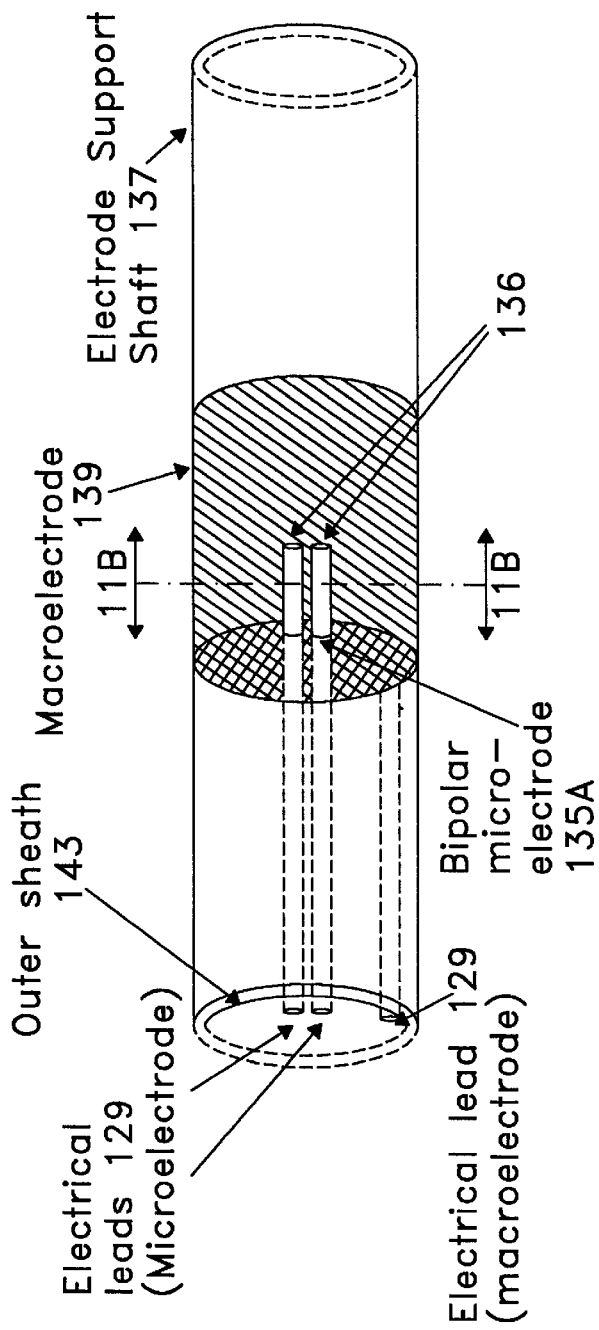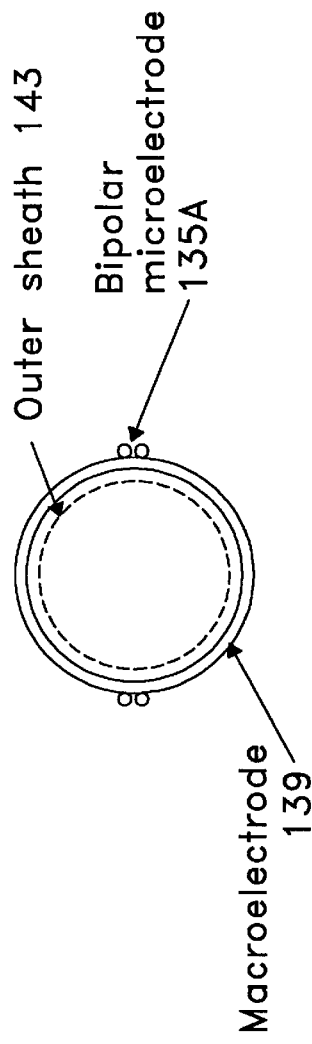

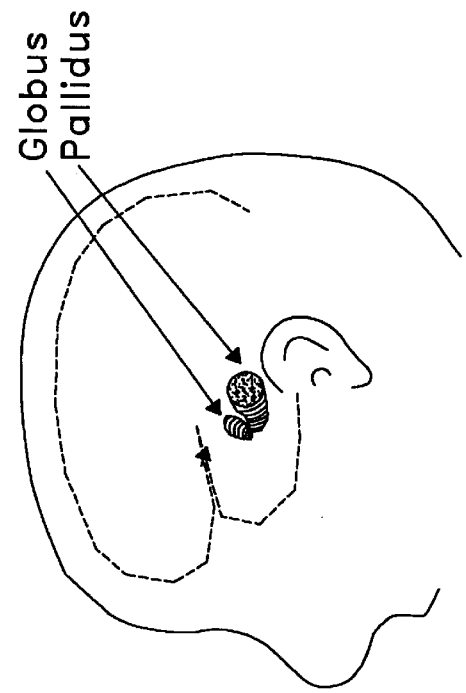
FIG. 12A
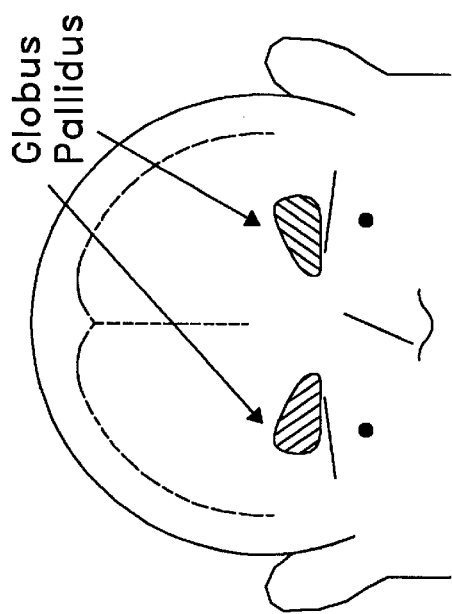
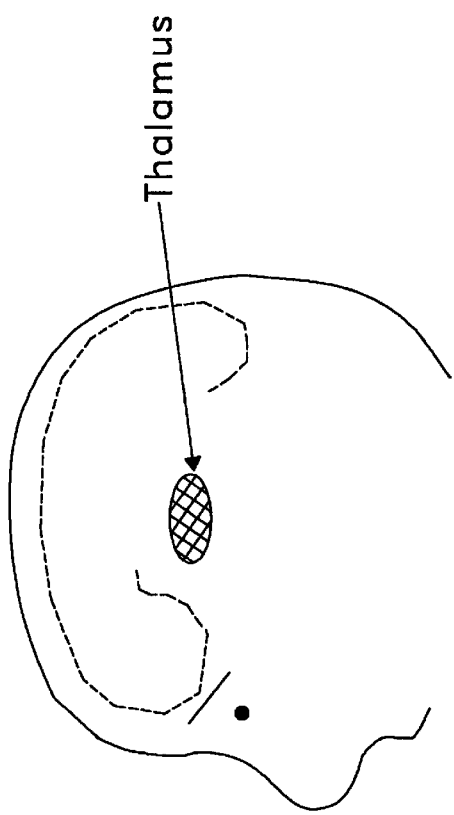
FIG. 12B

STEREOTACTIC ELECTRODE ASSEMBLY

RELATED U.S. APPLICATION DATA

This application is a continuation-in-part of U.S. patent application Ser. No. 08/194,017, filed Feb. 9, 1994, and issued as U.S. Pat. No. 5,469,369, which is a continuation-in-part of U.S. patent application Ser. No. 08/332,755, filed Nov. 1, 1994, pending, the contents of both of which are incorporated herein by reference.

BACKGROUND OF THE INVENTION

1. Field of the Invention

This invention relates generally to an apparatus and method for delivering and detecting electrical signals to/from the patient's brain.

In one embodiment, this invention also relates to an apparatus and method for performing ablative surgery on a patient. In particular the invention is concerned with an apparatus and method for performing brain surgery; and more particularly the invention is concerned with an apparatus and method for performing brain surgery by monitoring and selectively inactivating specific regions within the brain. The invention is also concerned with an apparatus and method for delivering therapeutic drugs, and more particularly is concerned with an apparatus and method for delivering therapeutic drug to a specific region within a patient's brain tissues, by monitoring and selectively delivering a drug to the target tissue.

2. Background of the Related Art

Prior to the nineteenth century, physicians and scientists believed the brain was an organ with functional properties distributed equally through its mass. Localization of specific functions within subregions of the brain was first demonstrated in the 1800s, and provided the fundamental conceptual framework for all of modern neuroscience and neurosurgery.

As it became clear that brain subregions served specific functions such as movement of the extremities, and touch sensation, it was also noted that direct electrical stimulation of the surface of these brain regions could cause partial reproduction of these functions. Morgan, J. P., "The first reported case of electrical stimulation of the human brain," *J. History of Medicine*, January 1982:51–63, 1982; Walker, A. E., "The development of the concept of cerebral localization in the nineteenth century," *Bull. Hist. Med.*, 31:99–121, 1957.

Brain Mapping Studies

The most extensive work on electrical stimulation "mapping" of the human brain surface was carried out over several decades by Dr. Wilder Penfield, a neurosurgeon and physiologist at the Montreal Neurological Institute, mostly during the early to mid-1900s. He made precise observations during cortical stimulation of hundreds of awake patients undergoing brain surgery for intractable epilepsy. Among his many findings, he noted that stimulation of the visual and hearing areas of the brain reproducibly caused the patients to experience visual and auditory phenomena. Penfield, W. et al., "Somatic motor and sensory representation in the cerebral cortex of man as studied by electrical stimulation," *Brain* 60:389–443, 1937; Penfield, W. et al., *Epilepsy and the Functional Anatomy of the Human Brain*, London: Churchill, 1954; Penfield, W. et al., "The brain's record of auditory and visual experience," *Brain*, 86:595–696, 1963. Following the results of early human brain mapping studies, electrical stimulation of sensory brain regions to restore lost function was a logical therapeutic extrapolation. Drs. Brindley and Lewin of the University of Cambridge were the first to reduce the concept to practice by implanting a patient with a visual cortex neural prosthetic device. Brindley, G. S. et al., "The sensations produced by electrical stimulation of the visual cortex," *J. Physiol.* 196:479–493, 1968. Their device consisted of an array of thin, flat electrodes placed on the surface of the visual cortex. The electrodes were remotely controlled with radio signals. A similar system was later tested at the University of Utah by Dr. Dobelle and colleagues. Dobelle, W. H. et al., "Artificial vision for the blind: stimulation of the visual cortex offers hope for a functional prosthesis," *Science* 183:440–444, 1974.

Findings from these early British and American studies were consistent. Patients reliably perceived flashes of light (phosphenes) during periods of electrical stimulation, and simple patterns of phosphenes could be generated by simultaneously activating multiple contacts. While these findings strongly suggested the eventual feasibility of a cortical visual prosthetic device, many important design problems were insurmountable at that time.

Among these were an inability to precisely stimulate very small volumes of brain, the requirement for high stimulation currents to induce phosphenes, and an inability to access the patient's full "visual space" with the large array of surface electrodes used. Additionally, there were no miniature video cameras and small, powerful computers at the time capable of converting visual images into complex electrical stimulation sequences at ultra high speed.

Penetrating Electrodes as Neural Prostheses

The University of Utah has discontinued visual cortex prostheses research. However, the concept has been pursued at NIH where significant additional advances have been made. Their most important discovery to date relates to the use of needle shaped penetrating depth electrodes instead of flat surface stimulating electrodes. Bak, M., et al., "Visual sensations produced by intracortical microstimulation of the human occipital cortex," *Med. Biol. Eng. Comput.*, 28:257–259, 1990. Penetrating electrodes represent a major design improvement. They are placed within the brain tissue itself so there is optimal surface contact with elements of the brain that are targeted for stimulation. As a result, patients perceive visual phosphenes with approximately a thousand-fold less stimulation current than that required when surface electrodes are used. This allows for safe, chronic stimulation of very small discrete volumes of brain.

Additionally, penetrating electrodes transform what was in the past a two dimensional implant-brain interface (flat disks on the surface of the brain) into a three dimensional interface (multiple needle-like electrodes in parallel extending from the surface into the brain substance), which vastly increases the device's access to stimulation targets below the surface. To use a television screen analogy, a two dimensional surface-electrode array may have the potential of generating an image on the "screen" composed of approximately one hundred discreet dots ("pixels"), whereas a three-dimensional array would potentially generate an image with many thousands of dots. The huge potential increase in image resolution would be achieved using a small fraction of the stimulation currents used in the past.

Penetrating electrodes have the potential to markedly increase both image quality and the safety of the stimulation process. Human experimental studies continue at the NIH campus. Extramural NIH funding is also directed at supporting engineering research on penetrating electrodes optimally suited for neural prosthetics applications. The University of Michigan, for example, has made use of computerchip manufacturing techniques to synthesize exquisitely small electrode arrays. The etched electrical contacts on these devices are so small that the distance separating adjacent contacts can be in the range of 50 micrometers, approximately the diameter of two nerve cell bodies. Drake, K. L. et al., "Performance of planar multisite microprobes in recording extracellular single-unit intracortical activity," *IEEE Trans. BME,* 35:719–732, 1988.

During the 1970s the neural prosthetics group at the University of Utah not only explored the feasibility of a visual cortex neural prosthetic device, but carried out experiments in auditory cortex stimulation as well. Led by Dr. Dobelle, they formed a mobile research group that traveled to surgical centers throughout the United States when suitable experimental subjects were identified. These were patients who required temporal lobe surgery for tumor removal or treatment of intractable epilepsy, and who agreed to participate in the experimental protocol. Dobelle, W. H. et al., "A prosthesis for the deaf based on cortical stimulation," *Ann. Otol,* 82:445–463, 1973.

The primary auditory region of the human brain is buried deep within the Sylvian fissure. It is not visible from the brain surface and its exact location varies slightly from one person to the next. MRI and CT scanners were not invented at the time of Dr. Dobelle's experiments so the anatomy of the patients' auditory cortex could not be studied prior to surgery, and this region could only be visualized with difficulty in the operating room after the Sylvian fissure was surgically dissected. Once the buried auditory cortex was exposed, surface stimulating electrodes were placed by hand over the area thought to be auditory cortex and the brain was stimulated in a fashion similar to that used to generate visual phosphenes.

Reproducible sound sensations were generated in the experimental subjects. Though these preliminary findings were encouraging, a range of limitations precluded further work by this group. Among the more daunting problems the Utah group faced were recruiting suitable patients for the experimental study and obtaining good stimulation characteristics from the experimental surface electrodes. The minimal stimulation threshold for eliciting sound sensations was found to be 6 milliamperes, which is too high to be tolerated chronically and is thousands of times greater than currents found subsequently to be required to generate phosphenes in visual cortex using penetrating electrodes.

Recent advances in MRI and computer technology now allow detailed preoperative imaging of human auditory cortex.

Another major technical innovation developed since the time of Dr. Dobelle's early experiments is the cochlear implant. An important aspect of the cochlear implant technology, which is now highly refined, involves transducing sound into complex electrical stimulation sequences. This large body of technical knowledge developed over the last twenty years will be directly applicable to the auditory cortex prosthetic device and aid immeasurably in its research and development.

Normal Hearing

Mechanisms of human hearing are reviewed briefly to provide a framework for discussion of auditory neural prosthetic devices. The auditory system is composed of many structural components that are connected extensively by bundles of nerve fibers. The system's overall function is to enable humans to extract usable information from sounds in the environment. By transducing acoustic signals into electrical signals that can then be processed in the brain, humans are able to discriminate amongst a wide range of sounds with great precision.

FIGS. 1A and 1B show a side and front view of areas involved in the hearing process. In particular, the normal transduction of sound waves into electrical signals occurs in cochlea 110, a part of the inner ear located within temporal bone (not shown). Cochlea 110 is tonotopically organized, meaning different parts of cochlea 110 respond optimally to different tones; one end of cochlea 110 responds best to high frequency tones, while the other end responds best to low frequency tones. Cochlea 110 converts the tones to electrical signals which are then received by cochlea nucleus 116. This converted information is passed from cochlea 110 into brain stem 114 by way of electrical signals carried along the acoustic nerve and in particular, cranial nerve VIII (not shown).

The next important auditory structure encountered is cochlea nucleus 116 in the brain stem 114. As the acoustic nerve leaves the temporal bone and enters skull cavity 122, it penetrates brain stem 114 and relays coded signals to cochlea nucleus 116, which is also tonotopically organized. Through many fiber-tract interconnections and relays (not shown), sound signals are analyzed at sites throughout brain stem 114 and thalamus 126. The final signal analysis site is primary auditory cortex 150 situated in temporal lobe 156.

The mechanisms of function of these various structures has also been extensively studied. The function of cochlea 110 is the most well-understood and the function of primary auditory cortex 150 is the least understood. For example, removal of the cochlea 110 results in complete deafness in ear 160, whereas removal of primary auditory cortex 150 from one side produces minimal deficits. Despite extensive neural connections with other components of the auditory system, primary auditory cortex 150 does not appear to be necessary for many auditory functions.

Cochlear Implant

Cochlear implants were designed for patients who are deaf as a result of loss of the cochlea's sound transduction mechanism. Implant candidates must have an intact acoustic nerve capable of carrying electrical signals away from the middle ear into the brain stem. The device converts sound waves into electrical signals which are delivered through a multi-contact stimulating electrode. The stimulating electrode is surgically inserted by an otolaryngologist into the damaged cochlea. Activation of the contacts stimulates acoustic nerve terminals which would normally be activated by the cochlear sound transduction mechanism. The patient perceives sound as the coded electrical signal is carried from the middle ear into the brain by the acoustic nerve. Cohen, N. L. et al., "A prospective, randomized study of cochlear implants," *N. Engl. J. Med.,* 328:233–7, 1993.

In patients with hearing loss caused by dysfunction at the level of the cochlea, cochlear implants can be remarkably effective in restoring hearing. For example, some previously deaf patients are able to understand conversations over the telephone following insertion of a cochlear implant.

Cochlear implants are surgically placed in the middle ear which is situated in the temporal bone. In patients who are already deaf, there is very little chance of any additional injury being caused by placement of a cochlear implant; they are very safe devices. Because of the low health risk associated with placing cochlear implants, obtaining experimental subjects during the early development stage was not difficult. In this setting design improvements occurred rapidly.

Cochlear Nucleus Implant

Patients are not candidates for cochlear implants if their hearing loss results from damage in auditory regions other than the cochlea. Because the first auditory relay station "downstream" from the cochlea and auditory nerve is the brainstem cochlear nucleus, this structure is a logical candidate for consideration as an implantation site. This approach was first developed at the House Ear Institute. Eisenberg, L. S. et al., "Electrical stimulation of the auditory brainstem structure in deafened adults," *J. Rehab. Res.* 24:9–22, 1987; Hitselberger, W. E. et al., "Cochlear nucleus implant," *Otolaryngol. Head Neck Surg.,* 92:52–54, 1984. As is the case with cochlear implants, sound waves are translated into a complex electrical code F. The implant's stimulation terminals are placed up against the cochlear nucleus, and the patient perceives sounds when the system is activated.

Data on efficacy is limited because relatively few patients have been tested with this device. Early findings demonstrate, however, that some degree of useful hearing is restored using this device. Environmental sounds such as a knock at the door and a telephone ringing have been detected by patients with a cochlear nucleus implant, and this improved auditory function has increased patients' ability to live independently.

Although work in the visual cortex demonstrates that central nervous system penetrating electrodes are significantly more effective than surface electrodes, use of penetrating electrodes in the cochlear nucleus has been discontinued for safety reasons described below.

For several reasons, there is significantly more risk associated with cochlear nucleus implants than cochlear implants. The cochlear nucleus is situated in the brain stem; a very sensitive and vital structure. Neurosurgical procedures in the brain stem are among the most difficult and dangerous operations performed. Infiltrating tumors within the substance of the brainstem, for example, are usually considered surgically inoperable. Surgical manipulation or injury of brainstem elements can cause devastating complications, including loss of normal swallowing functions, loss of control of eye movements, paralysis, coma, and death.

Because of their internationally renowned acoustic neuroma practice, doctors at the House Ear Institute are among the most experienced surgeons in the world at gaining surgical access to the brainstem surface. Acoustic neuromas are tumors arising from the supporting cells of the acoustic nerve. As they enlarge, these tumors expand into the cranial cavity and press up against the brainstem. Patients typically present with hearing loss, and a number of surgical approaches have been developed by otolaryngologists and neurosurgeons to remove these lesions.

Surgeons at the House Ear Institute have played a pioneering role in acoustic neuroma surgery and now routinely perform operations where the tumor is safely removed and the brainstem surface is visualized. They have placed cochlear nucleus implants in deaf patients who have lost function of both acoustic nerves and are undergoing removal of an acoustic neuroma. This affords access to the brainstem surface during a medically necessary procedure.

The first cochlear nucleus implant used penetrating electrodes. These functioned well initially, however within two months they had migrated further into the brainstem, causing tingling sensation in the patient's hip as adjacent fiber tracts were inadvertently stimulated. This system was removed and surface electrodes have been used for cochlear nucleus implants since that time. Risks of implanting a cochlear nucleus device are such that patients are only candidates for implantation if they require surgery in that area of the brainstem for some other, usually life threatening reason.

It is difficult to find suitable patients for implantation and testing of cochlear nucleus implants. The most likely candidates are patients who have a rare form of neurofibromatosis and acoustic neuromas on both acoustic nerves. Martuza, R. L. et al., "Neurofibromatosis 2 (Bilateral Acoustic Neurofibromatosis)," *N. Engl. J. Med.,* 318:684–688, 1988. A small number of these patients are referred regularly to such institutions as the House Ear Institute. Many university medical centers, however, would be unable to identify a single suitable candidate during a full year. In the fourteen years since its initial clinical application at the House Institute, cochlear nucleus implant use and testing has remained quite restricted (less than two implants per year average during the epoch reported in Eisenberg, L. S. et al., "Electrical stimulation of the auditory brainstem structure in deafened adults," *J. Rehab. Res.* 24:9–22, 1987.

Treating Deafness

Devices designed to treat deafness must take into consideration the underlying cause of deafness. For example, a patient with defective cochlea 110 who still has a functional acoustic nerve, may benefit from an artificial cochlea (cochlear implant). However, if the acoustic nerve is damaged and cannot carry electrical signals, then the problem is "too far downstream" in the signal processing sequence for a cochlear implant to be effective. In that situation, artificial signals must enter the auditory system "beyond the block" either in brain stem 114 or in auditory cortex 150.

Parkinson's Disease

Parkinson's disease is a neuropathological condition of unknown aetiology which afflicts approximately 1 million individuals in the U.S. alone. Symptoms include a paucity of spontaneous movement (bradykinesia), rigidity, and tremor, which in many cases can be very disabling. The average age of onset is 57, with about 30% of cases being diagnosed before age 50. Since the 1960's a number of different drugs have been used for the treatment of Parkinson's disease. Drug treatment of Parkinson's disease may ameliorate some of the symptoms, but does not provide a cure for the disease. Furthermore, drugs used for the treatment of Parkinson's disease tend to become less effective in alleviating symptoms over time and often result in severe side effects. For example, L-dopa which has been widely used for the treatment of Parkinson's disease over the past 30 years, is associated with side effects which include uncontrollable muscular contraction of the limbs and face. And, with the passage of time many, perhaps all, patients fail to respond well to L-dopa treatment.

Prior Art Surgical Treatment of Parkinson's Disease

Surgical treatment by neurosurgeons to treat Parkinson's disease has its roots in the observation that some patients exhibited decreased symptoms after experiencing a mild stroke. A widely accepted explanation for this observation is that the stroke caused destruction of fiber tracts or groups of neurons which had been conducting or generating abnormal signals. Early attempts to treat Parkinson's disease by selectively inactivating certain parts of the brain gave mixed results. The poor results obtained can be ascribed to a number of causes, particularly including poor targeting of brain tissue to be inactivated and imprecision in the design and use of the surgical probes.

Neurosurgeons at a number of medical centers worldwide are currently performing stereotactic thalamotomy or pallidotomy for the treatment of Parkinson's disease, in which regions within the target tissue (thalamus or globus pallidus) of the patient's brain are surgically accessed, physiologically monitored, and targeted for localized tissue destruction (Laitinen, L. Y., et al., "Leksell's posteroventral pallidotomy in the treatment of Parkinson's disease," *J. Neurosurg.*, 76:53–61, 1992; Iacono, R. P., et al., "The results, indications, and physiology of posteroventral pallidotomy for patients with Parkinson's disease," *Neurosurgery*, 36:1118–1127, 1995, and references cited therein).

FIG. 12A shows the gross morphology, relative size and approximate location of the globus pallidus. The globus pallidus is a conical subcortical structure which is involved in the control of movement. FIG. 12B shows the gross morphology, relative size and approximate location of the thalamus. The thalamus is a relatively large ovoid body which, inter alia, relays sensory stimuli to the cerebral cortex.

Prior art stereotactic pallidotomy

The currently used prior art procedure is quite complex and cumbersome. Briefly, it involves a preliminary step of obtaining microelectrode recordings from specific regions within the globus pallidus. Then, depending on the electrical potential(s) recorded from the particular region under study, the microelectrode is removed, and a macroelectrode is introduced into the same region of the globus pallidus to create a lesion thereat, thereby causing localized tissue destruction and irreversible inactivation of neurons in that region. This process must be repeated a number of times in order to obtain an appropriate "sample" of the globus pallidus.

According to the prior art stereotactic techniques, the trajectories of the introduced electrodes are perpendicular to the long axis of the globus pallidus, as shown in FIG. 12C. The prior art techniques therefore entail the surgeon making several passes through normal brain tissue. In addition, the electrode trajectories of the prior art techniques are the least useful with respect to sampling the target volume. Furthermore, the use of separate electrodes for monitoring neuron physiology (microelectrode) and for producing lesions (macroelectrode) is inefficient, time consuming, and is prone to error in positioning the macroelectrode.

SUMMARY OF THE INVENTION

It is an object of the instant invention to provide an apparatus comprising an introducer tube for introducing an electrode assembly into a specific region of a patient's brain.

It is a further object of the invention to provide an apparatus which comprises an electrode assembly having a rigid electrode support shaft bearing at least one neuron-monitoring bipolar microelectrode.

It is a further object of the invention to provide an electrode assembly which comprises at least one neuron-monitoring bipolar microelectrode, the electrical contacts of which are flexible.

It is a further object of the invention to provide an electrode assembly bearing at least one neuron-monitoring bipolar microelectrode, which can be used to obtain high quality recordings of action potentials of individual neurons chronically over a period of a number of days.

It is a further object of the instant invention to provide an apparatus which comprises a dual purpose electrode assembly which is used for both monitoring neuronal physiology and for chronic electrical stimulation of a target cell or target tissue.

It is a further object of the instant invention to provide an apparatus which comprises a dual purpose electrode assembly which is used for both monitoring neuronal physiology and for making lesions at the site of a target cell or target tissue.

It is a further object of the invention to provide a dual purpose multicontact neuron-monitoring and lesion-producing electrode assembly having a plurality of neuron-monitoring microelectrodes, and lesion-producing capability located at a plurality of sites on the electrode assembly, the sites of lesion-producing capability having a defined location relative to the location of the microelectrodes.

It is a further object of the invention to provide a dual purpose neuron-monitoring and lesion-producing electrode assembly having a plurality of neuron-monitoring microelectrodes and an equal number of adjacently located, spatially paired, or coincidental sites of lesion-producing capability.

It is still a further object of the invention to provide a dual purpose multicontact electrode assembly, with both neuron-monitoring and lesion-producing capability, having a magnetically tipped electrode support shaft for stereotactic placement of the electrode support shaft in a specific conformation within the target tissue, wherein the support shaft is positioned under remote control by means of an external magnetic field applied in the vicinity of the target tissue.

It is yet a further object of the invention to provide an apparatus for performing ablative surgery on a specific region of a patient's brain, comprising a magnetically tipped multicontact dual purpose electrode assembly having the capacity to both monitor individual neurons within the target brain tissue and to produce lesions at the site within the target tissue at which neurons were monitored.

It is a further object of the instant invention to provide an apparatus which comprises a dual purpose electrode assembly which is used for both monitoring neuronal physiology and for delivering therapeutic drugs to the site of a target cell or target tissue.

It is a further object of the invention to provide a dual purpose multicontact neuron-monitoring/drug delivery electrode assembly having a plurality of neuron-monitoring microelectrodes and a plurality of sites capable of delivering a drug located on the electrode assembly, the sites of drug delivery capability having a defined location relative to the location of the microelectrodes.

It is a further object of the invention to provide a dual purpose neuron-monitoring/drug delivery electrode assembly having a plurality of neuron-monitoring microelectrodes and an equal number of adjacently located, spatially paired, or coincidental sites of drug delivery capability.

It is still a further object of the invention to provide a dual purpose multicontact electrode assembly, with both neuron-monitoring and drug delivery capability, having a magnetically tipped electrode support shaft for stereotactic placement of the electrode support shaft in a specific conformation within the target tissue, wherein the support shaft is positioned under remote control by means of an external magnetic field applied in the vicinity of the target tissue.

It is yet a further object of the invention to provide a method for delivering therapeutic drugs to target tissue(s) of a patient in which a dual purpose multicontact neuron-monitoring/drug delivering electrode assembly is inserted into the target tissue, at least one cell of the target tissue is monitored for physiologic activity using microelectrodes, and subsequently, a suitable dose of a therapeutic drug may be selectively delivered from a specific site on the electrode assembly to the specific region of the target tissue which was monitored.

It is a further object of the invention to provide a method for delivering therapeutic drugs to target tissue(s) of a patient, in which a dual purpose multicontact neuron-monitoring/drug delivering electrode assembly is inserted into the target tissue, the exact location and orientation of the target tissue being determined by computer assisted tomography (CT) scan and/or 3-dimensional magnetic resonance imaging (MRI).

It is yet a further object of the invention to provide a method for delivering therapeutic drugs to target tissue(s) of a patient, in which a dual purpose multicontact neuron-monitoring/drug delivery electrode assembly having a magnetic tip is moved to an appropriate position within the target tissue by the application of a magnetic field outside the patient's body part undergoing therapy.

It is still a further object of the invention to provide a dual purpose neuron-monitoring/drug delivery electrode assembly having at least one neuron-monitoring microelectrode, and at least one drug delivery port for the delivery of therapeutic drugs to specific, previously-monitored, sites within target tissue(s), the at least one drug delivery port having a defined location on the electrode assembly relative to the location of the microelectrodes.

It is yet a further object of the invention to provide a method for performing a ablative surgery on a specific region of a patient's brain, in which a dual purpose multicontact electrode assembly is inserted into the target tissue, a plurality of neurons are monitored for physiologic activity using microelectrodes, and subsequently, without moving the microelectrodes, one or more macroelectrodes may be selectively activated or energized to form lesions within the target tissue at the site of the specific neurons which were monitored.

It is a further object of the invention to provide a method for performing ablative surgery on a specific region of a patient's brain, in which a dual purpose multicontact electrode assembly is inserted into the target tissue, the exact location and orientation of the target tissue being determined by computer assisted tomography (CT) scan and/or 3-dimensional magnetic resonance imaging (MRI).

It is yet a further object of the invention to provide a method for performing ablative surgery, in which a dual purpose multicontact electrode assembly having a magnetic tip is moved to an appropriate position within the target tissue by the application of a magnetic field outside the patient's body part undergoing surgery.

Another object of the invention is to provide a prosthetic which can be placed in a cerebral cortex to reconstitute sensor input to the brain using microstimulation.

It is still a further object of the invention to provide a neural prosthesis comprising a multicontact electrode assembly which has a magnetic tip for stereotactic placement of the electrode assembly within auditory cortex.

It is still a further object of the invention to provide a multicontact electrode assembly which has a magnetic tip for stereotactic placement of the electrode assembly within the target tissue by means of applying an external magnetic field in the vicinity of the target tissue.

It is a further objective of the invention to provide a method for positioning a neural prosthesis having a magnetic tip in an appropriate conformation within the auditory cortex.

Another object of the invention is to provide a prosthetic which can be positioned in the brain such that an entire range of tonal frequencies processed by the human brain are accessed thereby.

Another object of the invention is to provide a prosthetic which allows a physician to physiologically test location and function of neural prosthetic electrodes in patients undergoing surgery for medically intractable epilepsy.

One feature of the invention is that it includes a penetrating longitudinal support or electrode.

Another feature of the invention is that it can include a plurality of electrical contacts on the longitudinal support.

Another feature of the invention is that it includes a speech processor.

Another feature of the invention is that each electrode on the electrode support can separately and independently introduce electrical discharges in the brain.

Another feature of the invention is that it is arranged along the auditory cortex.

Another feature of the invention is that it can include a flexible multicontact electrode support.

Another feature of the invention is that the flexible multicontact electrode support is inserted into the brain using a rigid introducer.

Another feature of the invention is that a flat plastic plate attached to the longitudinal support helps position the prosthetic in the auditory cortex, the flat plastic plate having a cup to receive a sphere coupled to leads which interconnect the contacts to the speech processor.

One advantage of the invention is that it includes contacts which enable a deaf patient to hear even though the patient's problem is not in his or her cochlear regions but instead is farther "down stream."

Another advantage of the invention is that it can utilize a single electrode or electrical contact mounted on an electrode support.

Another advantage of the invention is that it penetrates the brain, thus requiring a smaller, more readily tolerable current to stimulate localized regions of the auditory cortex, compared to the amount of current required during stimulation of the brain surface.

Another advantage of the invention is that the contacts are sufficiently closely arranged next to each other to provide high resolution stimulation of the auditory cortex.

These and other objects, advantages and features are accomplished by the provision of a neural prosthetic device for an auditory cortex of a patient, including: a speech processor for receiving and processing audio information and for outputting processed electrical signals; a support arranged in the auditory cortex having a plurality of electrical contacts independently outputting electrical discharges in accordance with the processed electrical signals; and electrical coupling means for electrically coupling the electrical contacts to the speech processor.

The above objects, advantages and features are further accomplished by the neural prosthetic apparatus as above, wherein the support is arranged in the auditory cortex and the plurality of electrical contacts are arranged such that the plurality of electrical contacts approximately tonotopically match the auditory cortex.

These and other objects, advantages and features are also accomplished by a method of implanting the above support, including the steps of: acquiring a 3-dimensional digital image of the patient's brain and storing the 3-dimensional digital image in a memory of a computer; digitally subtracting data from the 3-dimensional digital image to yield a modified 3-dimensional digital image which shows the orientation of the auditory cortex in the patient's brain; and inserting the support into the auditory cortex using the modified 3-dimensional digital image as a guide.

The above and other objects, advantages and features are further accomplished by the steps of: repeatedly outputting the processed electrical signals to the plurality of electrical contacts; and adjusting orientation of the support in the auditory cortex as the patient describes effects of the repeatedly outputting step.

One feature of the invention is that it can include a penetrating longitudinal support shaft bearing a single microelectrode for monitoring physiologic activity of a cell.

Another feature of the invention is that it can include a penetrating longitudinal support shaft bearing multiple microelectrodes for monitoring physiologic activity.

Another feature of the invention is that each microelectrode for monitoring physiologic activity can be bipolar.

Another feature of the invention is that each neuron-monitoring microelectrode of the electrode assembly can independently monitor the physiological activity of the neuron(s) with which it makes contact.

Another feature of the invention is that each lesion-producing macroelectrode of the electrode assembly can be independently energized to produce a localized lesion.

Another feature of the invention is that the electrode support shaft of the electrode assembly can be rigid.

Another feature of the invention is that the electrode support shaft of the electrode assembly can be flexible.

Another feature of the invention is that it can include a magnet at its distal end.

Another feature of the invention is that the flexible support shaft can be positioned generally along the long axis of the globus pallidus.

Another feature of the invention is that the multicontact electrode support shaft is introduced into the brain using a stereotactically inserted introducer tube.

One advantage of the invention is that it can function with a single electrode support shaft.

Another advantage of the invention is that it allows the neuron-monitoring and lesion-producing functions of prior art pallidotomy to be performed by the same electrode assembly.

Another advantage of the invention is that the microelectrode and macroelectrode contacts are sufficiently small and closely arranged on the electrode support shaft to enable high resolution monitoring and inactivation of the target tissue.

Another advantage of the invention is that it reduces the chances for error in placement of electrodes during surgical procedures by eliminating the need to use separate neuron-monitoring and lesion-making electrode assemblies.

Another advantage of the invention is that it allows the monitoring of a plurality of neurons and the subsequent production of a plurality of lesions following a single placement of the electrode support shaft within the target tissue.

Another advantage of the invention is that the neuron-monitoring microelectrodes and lesion-producing macroelectrodes are sufficiently small and closely arranged next to each other to enable a high degree of spatial correlation between neuron monitoring and neuron inactivation functions.

Another advantage of the invention is that the electrode support shaft can be retrieved from a given position within the brain to the introducer tube by exerting a force on a tether line.

Yet a further advantage of the invention is that the magnetically tipped electrode support shaft can be positioned in a desired spatial orientation within the brain by changing the magnitude and direction of magnetic forces which urge the electrode support shaft forwards.

These and other objects, advantages and features are accomplished by the provision of an apparatus for performing surgery on a patient, including: an electrode assembly comprising an electrode support shaft bearing a plurality of spatially paired or coincidental microelectrodes and macroelectrodes, and an introducer tube for introducing the electrode support shaft into the patient. The electrode assembly also comprises a tether line for retrieving the electrode assembly from the target tissue.

These and other objects, advantages and features are accomplished by a method of performing surgery on a patient, including the steps of: introducing the distal end of the electrode support shaft into the target tissue, monitoring a plurality of neurons therein for their physiologic response, and subsequently selectively energizing one or more spatially paired or coincidental lesion-producing macroelectrodes according to the response recorded from the plurality of microelectrodes.

These and other objects, advantages and features are accomplished by a method of performing surgery on a patient, comprising the steps of: stereotactically inserting an introducer tube into the brain of a patient such that the distal end of the tube is positioned close to the target tissue, introducing an electrode assembly into the introducer tube, the electrode assembly comprising an electrode support shaft bearing a magnetic tip responsive to an external magnetic field, driving the magnetic tip of the electrode assembly through a defined trajectory within the globus pallidus, monitoring the physiological activity of at least one neuron within the globus pallidus, optionally, according to the monitoring of the physiological activity, inactivating the at least one neuron by activating the at least one macroelectrodes.

These and other objects, advantages and features are accomplished by the provision of an apparatus for performing pallidotomy on a patient, including: an electrode assembly having a magnetically tipped, flexible electrode support shaft bearing a plurality of spatially paired microelectrodes and macroelectrodes, respectively for monitoring and inactivating specific neurons or groups of neurons, and an introducer tube for introducing the electrode support shaft into the patient. The electrode assembly also comprises a tether line for retrieving the electrode assembly from the target tissue. The electrode assembly may then be repositioned in the home position within the introducer tube.

These and other objects, advantages and features are accomplished by a method of performing a pallidotomy on a patient including the steps of: introducing the distal end of the electrode support shaft into the globus pallidus, monitoring a plurality of neurons therein for their physiologic response using a plurality of neuron-monitoring microelectrodes, and subsequently selectively energizing one or more spatially paired lesion-producing macroelectrodes according to the response recorded from the plurality of microelectrodes.

These and other objects, advantages and features are accomplished by a method of performing pallidotomy on a patient, comprising the steps of: stereotactically inserting an introducer tube into the brain of a patient such that the distal end of the tube is positioned close to the lateral globus pallidus; introducing an electrode assembly into the introducer tube, the electrode assembly comprising an electrode support shaft, the electrode support shaft having a magnetic distal end responsive to an external magnetic field and further bearing at least one neuron-monitoring microelectrode and at least one lesion-producing macroelectrode spatially paired with the at least one microelectrode; driving, by the application of an external magnetic field, the magnetic end of the electrode assembly through a defined trajectory within the globus pallidus; monitoring the physiological activity of at least one neuron with the at least one microelectrode; optionally, according to the monitoring of the physiological activity, inactivating the at least one neuron by applying lesion-forming energy to the at least one neuron via the at least one macroelectrode; and assessing the patient's response to the above steps.

These and other objects, advantages and features are accomplished by a method of making a dual purpose multicontact electrode assembly capable of monitoring and inactivating neurons, comprising the steps of: arranging a plurality of electrical contacts along the longitudinal axis of an electrode support shaft, and coupling each of the electrical contacts to at least one strand of electrically conductive material, whereby a suitable electric current may be conducted to or from each of the electrical contacts.

These and other objects, advantages and features are accomplished by a method of making a dual purpose multicontact electrode assembly, comprising the steps of: providing an electrode support shaft having a distal end and a proximal end, positioning a plurality of neuron-monitoring microelectrodes along the distal end of the electrode support shaft, and positioning each one of a plurality of lesion-producing macroelectrodes adjacent to each one of the plurality of microelectrodes, and affixing a magnet, responsive to an applied external magnetic field, to the distal end of the support shaft.

These and other objects, advantages and features are accomplished by a method of making an introducer tube, comprising the steps of: providing a cylinder, rigidly attaching coaxially a conical neck to one end of said cylinder, the conical neck having a free end and the diameter of the conical neck having the same diameter as the cylinder at the point of juncture, the diameter of the conical neck increasing in the direction away from the cylinder, rigidly attaching coaxially a cylindrical end piece to the free end of the conical neck, the end piece having the same diameter as the free end of the conical neck, and providing sealing means for sealing the cylindrical end piece.

These and other objects, advantages and features are accomplished by provision of an introducer tube for introducing a device into the body of a patient, comprising: a cylindrical portion, a conical neck portion continuous with the cylindrical portion, a short cylindrical end piece continuous with the conical neck portion, and sealing means for sealing the proximal end of the introducer tube.

These and other objects, advantages and features are accomplished by provision of an apparatus for selectively inactivating neurons in a target tissue, comprising: an electrode support shaft, at least one lesion-producing macroelectrode arranged on the support shaft, and at least one neuron-monitoring microelectrode arranged on the support shaft, each one of the at least one microelectrodes having a defined location on the support shaft relative to the location of the at least one macroelectrode.

These and other objects, advantages and features are accomplished by provision of an apparatus comprising: a support shaft, at least one lesion-producing macroelectrode arranged along the support shaft for producing a lesion, and multiple neuron-monitoring microelectrodes arranged along the support shaft having a defined relative location on the shaft with respect to the at least one lesion-producing macroelectrode, the multiple neuron-monitoring microelectrodes monitoring neuronal activity and outputting signals which are used to determine whether to energize the at least one lesion-producing macroelectrode to produce the lesion.

These and other objects, advantages and features are accomplished by provision of an apparatus for making one or more lesions in a brain, comprising: an electrode support shaft, at least one lesion-producing macroelectrode disposed on the support shaft, and a fluid-coated introducer tube for introducing the support shaft into the brain, thereby allowing the lesion-producing macroelectrode to make the one or more lesions in the brain.

These and other objects, advantages and features are accomplished by provision of an apparatus, comprising: a flexible electrode assembly including an electrode support shaft, the support shaft having a magnetic tip which is responsive to an external magnetic field, one or more lesion-producing macroelectrodes arranged along the support shaft, an introducer tube for introducing the support shaft into a brain, and multiple neuron-monitoring microelectrodes arranged along the support shaft having a defined location on the support shaft relative to the one or more lesion-producing electrodes, the multiple neuron-monitoring microelectrodes monitoring neuronal activity and outputting signals which are used to determine whether to energize the one or more lesion-producing macroelectrodes.

These and other objects, advantages and features are accomplished by provision of an apparatus for producing one or more lesions at one or more locations in a globus pallidus of a human brain, comprising: a flexible electrode support shaft, a plurality of lesion-producing macroelectrodes arranged along the support shaft, and a plurality of neuron-monitoring microelectrodes arranged along the support shaft for outputting neuron activity signals, wherein the support shaft is draped along the globus pallidus and selective ones of the lesion-producing contacts are energized, in accordance with the neuron activity signals, to produce the at least one lesion in the globus pallidus.

These and other objects, advantages and features are accomplished by provision of an apparatus for delivering one or more therapeutic drugs to target tissue of a brain, comprising: a support shaft, at least one drug delivery site capable of delivering a therapeutic drug arranged along the support shaft, and multiple neuron-monitoring microelectrodes arranged along the support shaft having a defined relative location on the shaft with respect to the at least one drug delivery site, the multiple neuron-monitoring microelectrodes monitoring neuronal activity and outputting signals which are used to determine whether to deliver a therapeutic drug from the at least one drug delivery site to the target tissue.

These and other objects, advantages and features are accomplished by a method of delivering one or more therapeutic drugs to specific locations within the brain of a patient, comprising the steps of: stereotactically inserting an introducer tube into the brain of a patient such that the distal end of the tube is positioned close to the target tissue; introducing an electrode assembly into the introducer tube, the electrode assembly comprising an electrode support shaft, the electrode support shaft bearing a magnetic tip responsive to an external magnetic field and further bearing at least one neuron-monitoring microelectrode and at least one drug delivery site capable of delivering a measured dose of a therapeutic drug, the at least one drug delivery site being spatially paired with the at least one microelectrode;

moving, by the application of an external magnetic field, the magnetic tip of the electrode assembly to a defined location within the target tissue; monitoring the physiological activity of at least one neuron with the at least one microelectrode; and, optionally according to the monitoring of the physiological activity, delivering a measured dose of a therapeutic drug from the at least one drug delivery site.

These and other objects, advantages and features are accomplished by provision of a neural prosthetic device for a auditory cortex of a patient, the neural prosthetic device connected to a speech processor for receiving and processing audio information and for outputting processed electrical signals, and electrical coupling means for electrically coupling the plurality of electrical contacts to the speech processor.

These and other objects, advantages and features are accomplished by a method of implanting the support of the paragraph immediately above having a plurality of electrical contacts, comprising the steps of: acquiring a 3-dimensional digital image of the patient's brain and storing the 3-dimensional digital image in a memory of a computer, digitally subtracting data from the 3-dimensional digital image to yield a modified 3 dimensional digital image which shows the orientation of the auditory cortex in the patient's brain, inserting the support into the auditory cortex using said modified 3 dimensional digital image as a guide, repeatedly outputting processed electrical signals to the plurality of electrical contacts, and adjusting the orientation of the support in the auditory cortex, according to the patient's response to at least some of the processed electrical signals, the orientation of the support being controlled by adjustment of an applied external magnetic field.

These and other objects, advantages and features are accomplished by provision of an apparatus for selectively inactivating cells in a target tissue, comprising: an electrode support shaft, at least one cell-monitoring microelectrode arranged on the support shaft, and at least one lesion-producing macroelectrode arranged on the support shaft, each one of the at least one macroelectrode having a defined location on the support shaft relative to the location of the at least one microelectrode.

These and other objects, advantages and features of the present invention will become more apparent from the following description of embodiments thereof, taken in conjunction with the accompanying drawings.

BRIEF DESCRIPTION OF THE DRAWINGS

FIGS. 11A and 11B show details of an embodiment of a dual purpose electrode assembly bearing bipolar microelectrodes, in which the pair of electrical contacts of the microelectrodes are closely juxtaposed, and are positioned coincidental with, and external to, the macroelectrodes.

FIG. 12A shows (arrows) the approximate location and orientation, gross morphology, and relative size of the globus pallidus.

FIG. 12B shows (arrow) the approximate location and relative size of the thalamus.

FIG. 13A shows an introducer tube positioned within the patient's skull pointing generally in the direction of the globus pallidus. FIG. 13B shows the electrode assembly ex situ. FIG. 13C shows the electrode assembly within the introducer tube with the sealing cap unattached.

DETAILED DESCRIPTION OF THE PREFERRED EMBODIMENTS

There now follows a description of a neural prosthesis apparatus, under the invention, as well as methods of using the same. There then follows a description of apparatus and methods for performing stereotactic manipulations, including magnetic surgery and targeted drug delivery, according to the invention.

Neural Prosthesis

Advanced imaging combined with an intraoperative stereotactic system now enable placement of penetrating electrodes into auditory cortex during routine epilepsy surgery without dissection of the Sylvian fissure.

Figures 1A, 1B:
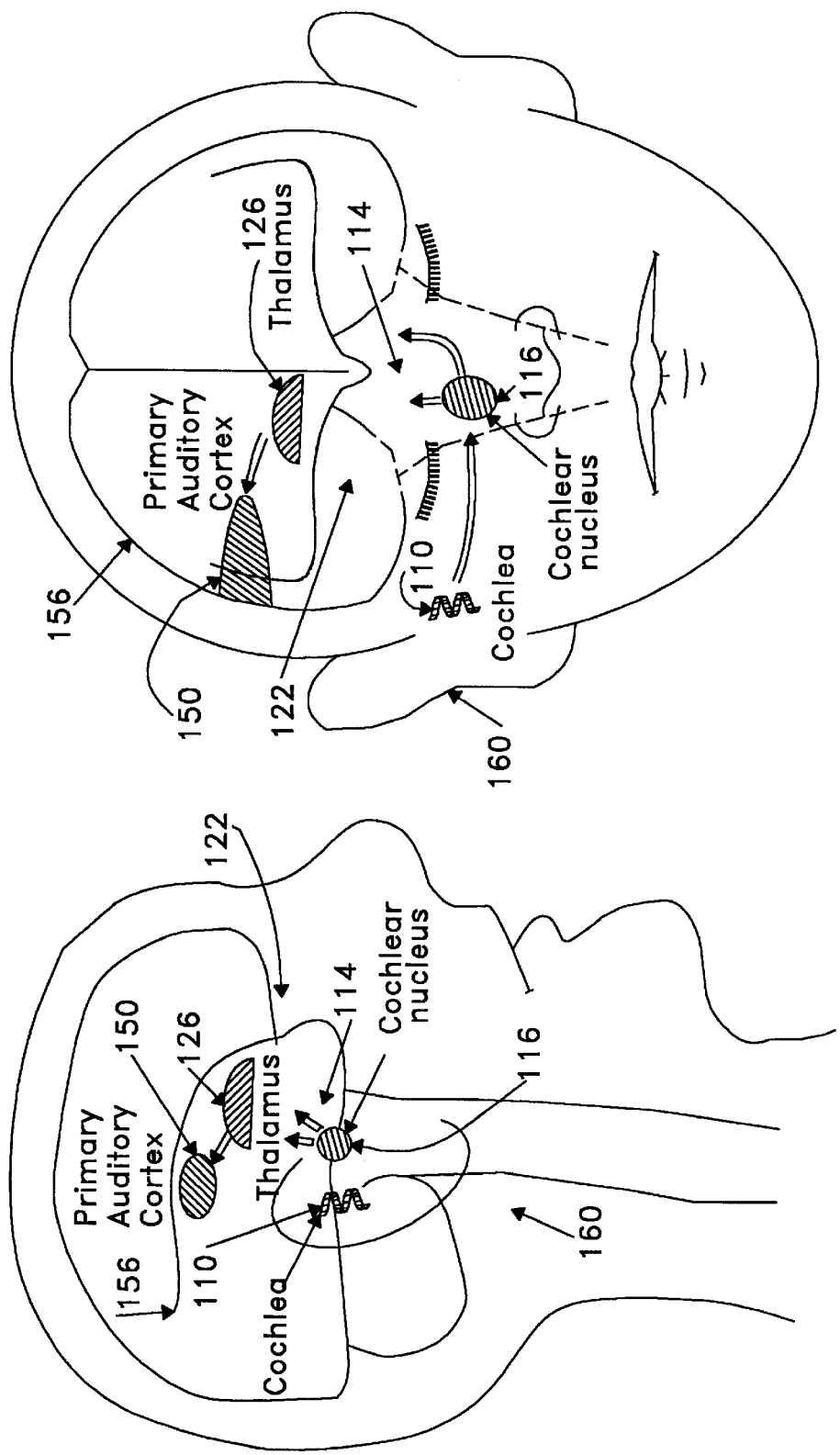
FIGS. 1A and 1B show the orientation of a patient's auditory cortex in relation to the patient's cochlea and cochlear nucleus.

Primary auditory cortex 150 in FIGS. 1A and 1B is tonotopically organized, meaning stimulation in different areas is likely to cause the patient to perceive different tones. These tones form the building blocks of complex sound phenomena such as speech. Tonotopic organization is a fundamental characteristic of the cochlea and cochlear nucleus as well, as discussed above. Primary auditory cortex 150, however, has its tonotopic map stretched across a larger volume of tissue (greater that twice the volume of cochlear nucleus 116). Greater tissue volume enables placement of a greater number of electrical contacts for a given tonotopic zone. This results in increased signal resolution and improved clarity of auditory sensation. Finally, because of anatomical differences, primary auditory cortex 150 can accommodate penetrating electrode arrays which cannot be safely placed into the cochlear nucleus.

Figure 2:
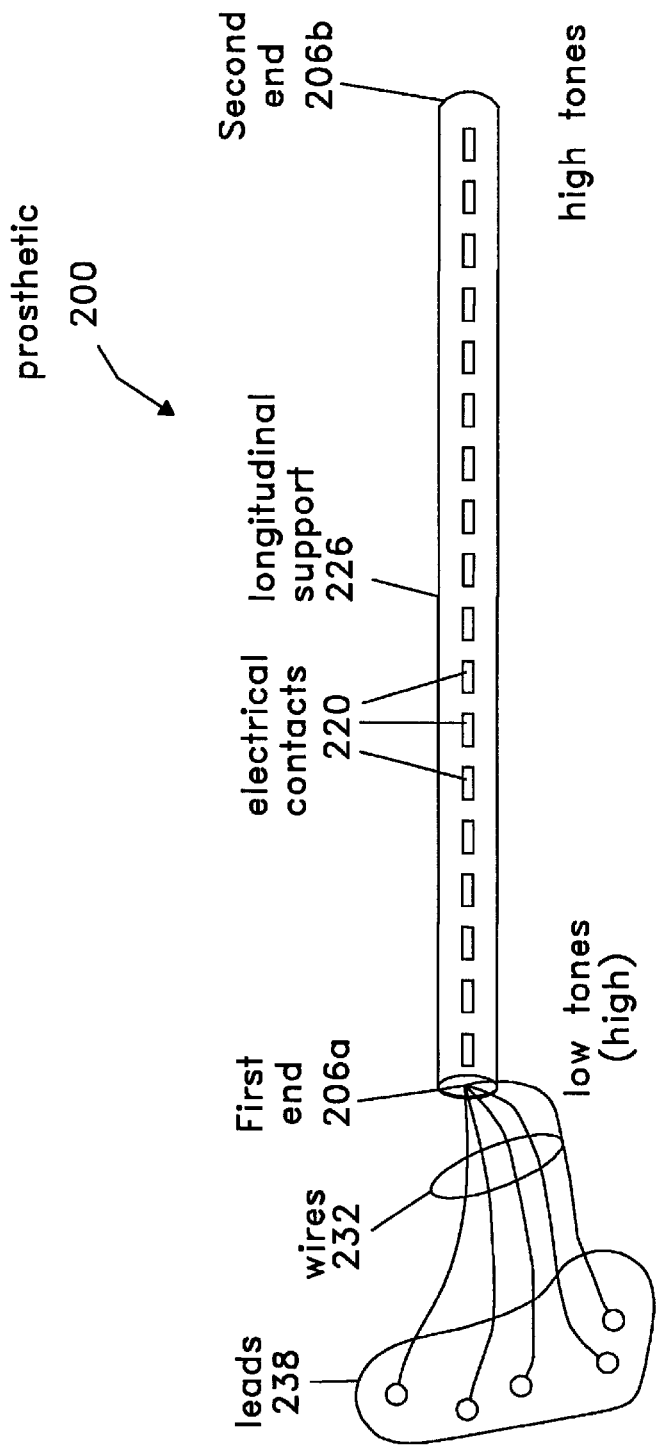
FIG. 2 shows a human cerebral cortex neural prosthetic.

FIG. 2 shows a human cerebral cortex neural prosthetic 200 according to one embodiment of the invention. Prosthetic 200 has a first end 206a and a second end 206b which is blunt or smoothly curved. Prosthetic 200 has electrical contacts 220 along a longitudinal support 226. Support 226 can be anywhere from several millimeters long to several centimeters long. Electrical contacts 220 are small metal pads which can be separately and independently electrically charged via respective wires 232 available at first end 206a. Wires 232 have leads 238 which are coupled to a speech processor (not shown). Electrical contacts 220 are spaced approximately 10 micrometers to several millimeters apart and preferably approximately 50 to 150 micrometers apart. Application of a voltage to contacts 220 near first end 206a results in stimulating low (or high–to be determined by questioning the patient) tones in primary auditory cortex 150 (see FIGS. 1A and 1B), whereas application of a voltage to contacts 220 near second end 206b results in stimulation of high (or low) tones in primary auditory cortex 150.

Longitudinal support 226 can be rigid or flexible. Prosthetic 200 may be introduced into a patient's brain via a rigid introducer, and subsequently electrical contacts 220 are exposed to primary auditory cortex 150. Support 226 can be one of the probes shown in FIGS. 3–5 in "Possible Multichannel Recording and Stimulating Electrode Arrays: A Catalog of Available Designs" by the Center for Integrated Sensors and Circuits, University of Michigan Ann Arbor, Mich., the contents of which are incorporated herein by reference. Alternative electrodes such as Depthalon Depth Electrodes and interconnection cables from PMT Corporation 1500 Park Road, Chanhassen, Minn., 55317 could also be used as support 226 and electrical couplers between contacts 220 and a speech processor (410 in FIG. 4).

Electrical contacts 220 must operate as high impedance (megohms) contacts as opposed to low impedance (a few ohms to several thousand ohms) contacts. This makes it possible to output a greater potential for the contacts while outputting a small (a few microamperes as opposed to a few milliamperes) current. This also localizes the potentials applied to the patient's auditory cortex to approximately a few hundred micrometers. The localization of applied electric charges corresponds to the tonotopic spacing of nerve cell pairs.

Prosthetic 200 is arranged along a longitudinal direction of primary auditory cortex 150. However, primary auditory cortex150 is located in the transverse temporal gyro and is buried deep within the Sylvian fissure. Consequently, its location cannot be determined simply by looking at an exposed surface of the brain. Therefore, MRI imaging techniques must be employed to reveal the exact orientation of primary auditory cortex 150.

A single coronal image of an individual's brain cannot reveal the exact orientation of primary auditory cortex 150. Instead, a series of images must be obtained and a resulting 3-dimensional MRI image constructed. Once such an image is constructed, the digital data making up that image can be transformed to provide a view of the Sylvian fissure. This in turn exposes primary auditory cortex 150 as a mound-like hump. That is, tissue on top of the digital image can be "peeled off" to expose the Sylvian fissure and consequently primary auditory cortex 150 "pops out" of the image. This process is described in "Three-dimensional In Vivo Mapping of Brain Lesions in Humans", by Hanna Damasio, M.D., Randall Frank, the contents of which are incorporated herein by reference.

Figure 3A:
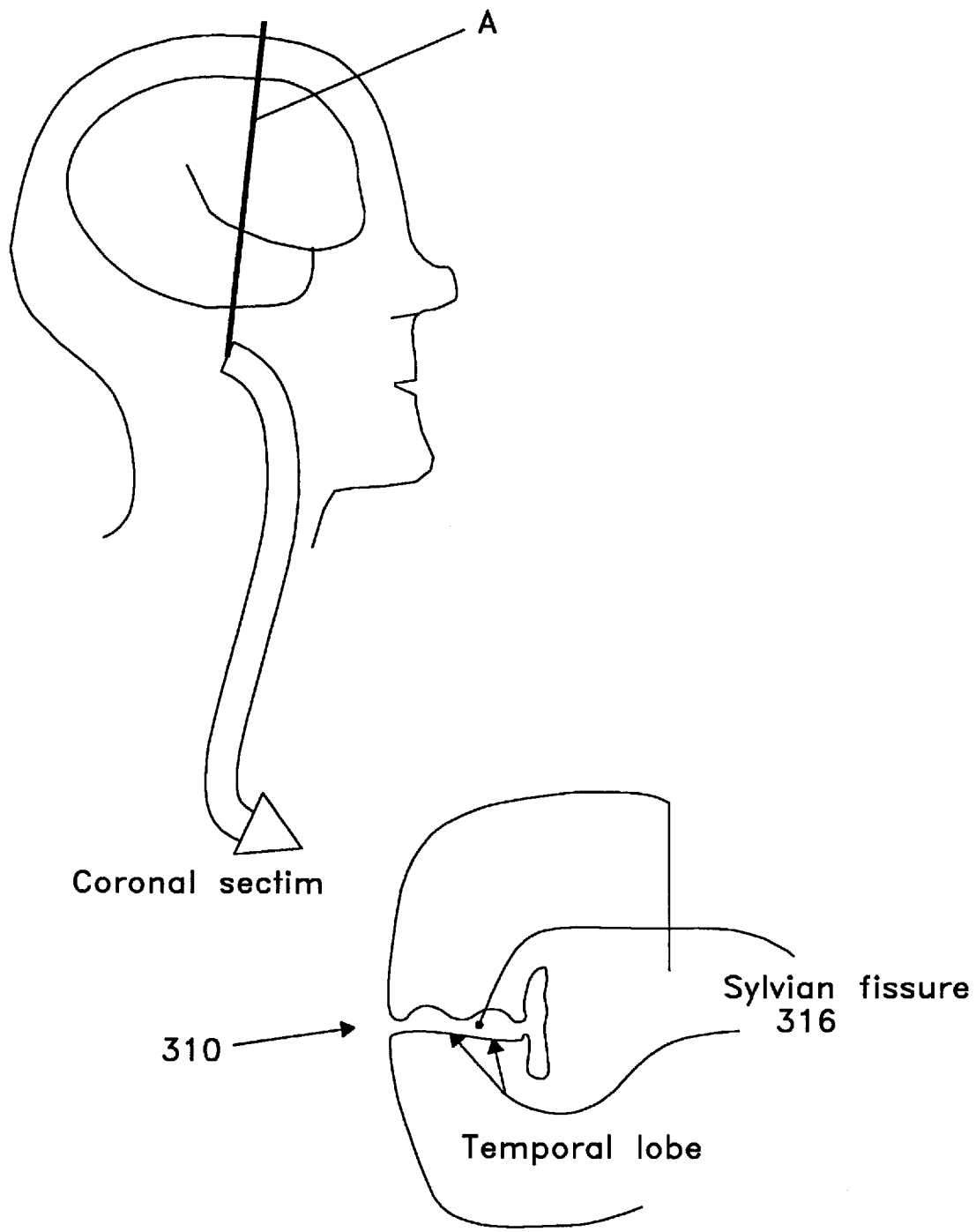
FIG. 3A shows a side view of a plane A which intersects a coronal section with a Sylvian fissure exposed.
Figure 3B:
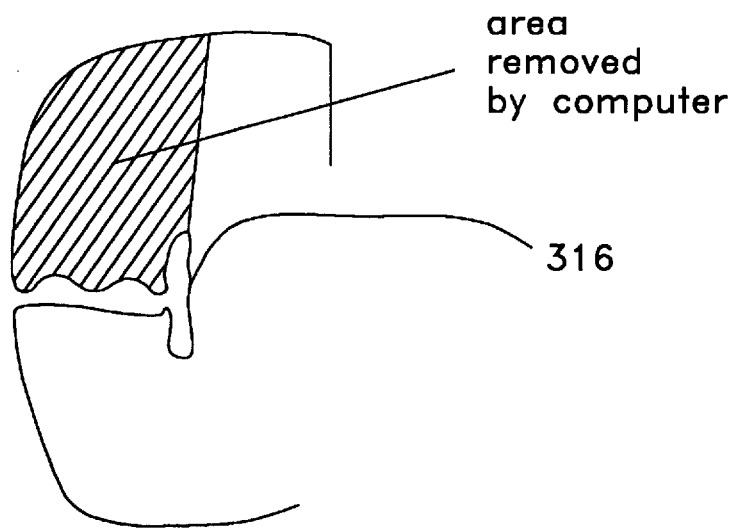
FIGS. 3B and 3C show the coronal section before and after tissue is digitally "peeled off" the Sylvian fissure.
Figure 3C:
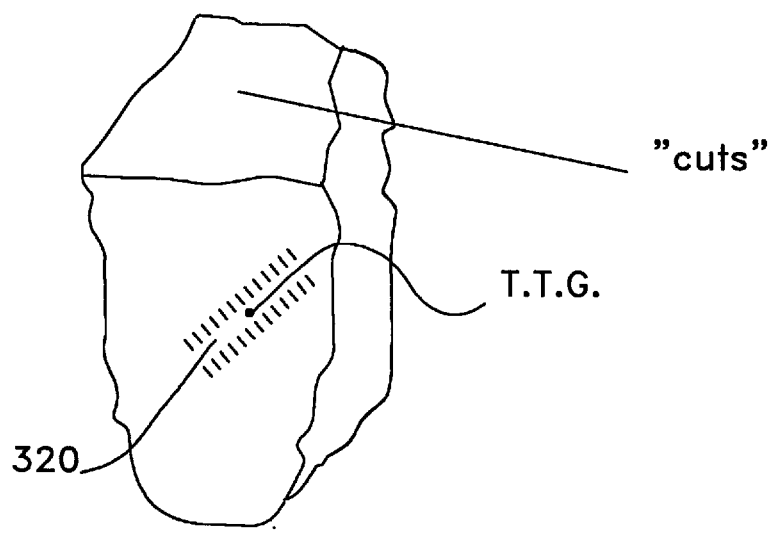

FIG. 3A shows a side view of a plane A which intersects a coronal section 310 as well as a view of coronal section 310 with Sylvian fissure 316 exposed. FIGS. 3B and 3C show coronal section 310 before and after tissue is digitally "peeled off" to expose primary auditory cortex 150. One or more resulting mounds 320 is revealed in FIG. 3C and this mound corresponds to primary auditory cortex 150 of FIG. 1B. Mound 320 does not appear until after tissue on the underside of Sylvian fissure 316 is reconstructed to provide the 3-dimensional image.

Figure 4:
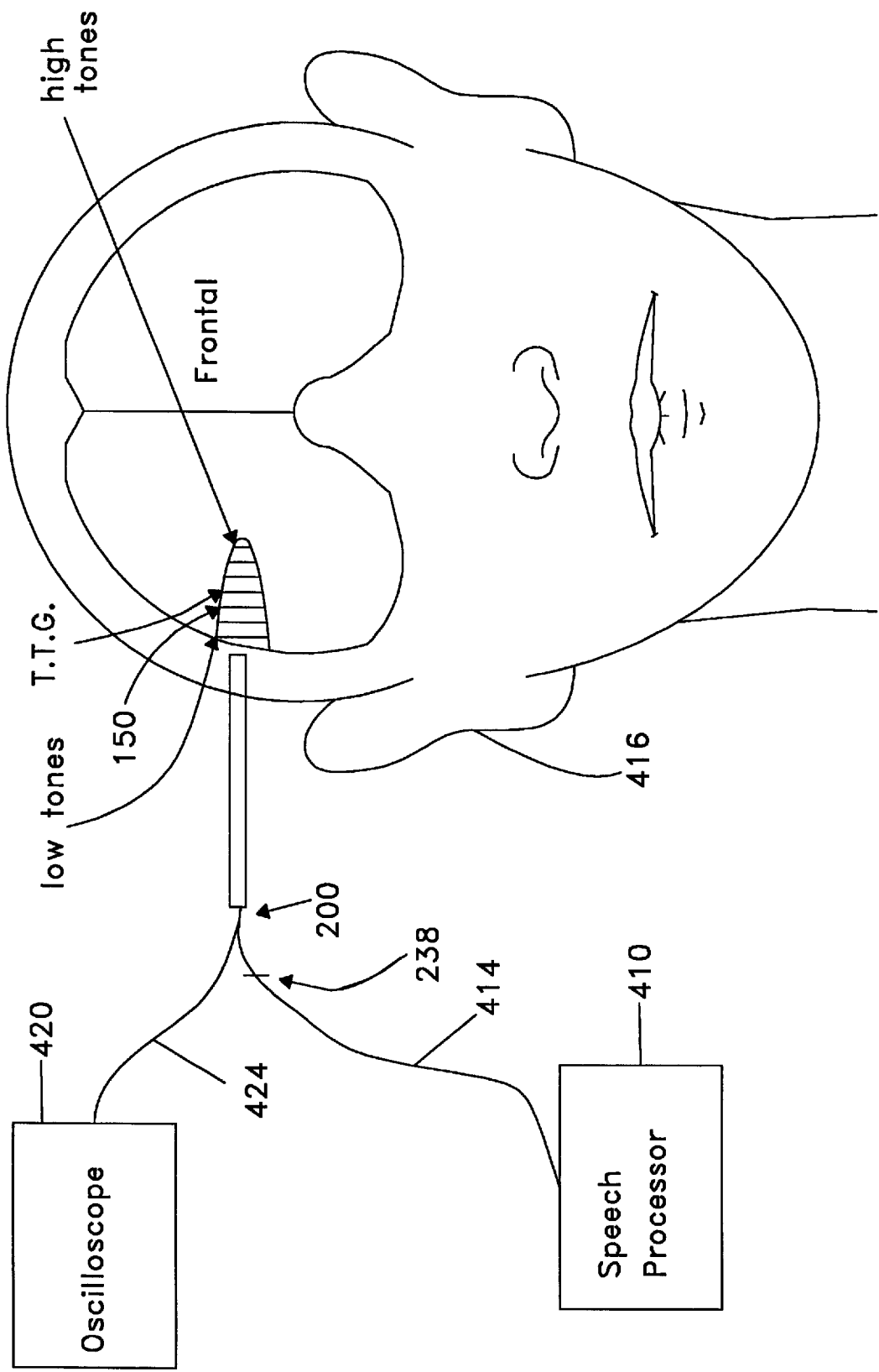
FIG. 4 shows a neural prosthetic with a support having electrical contacts and its speech processor.

Once the exact location and orientation of mound 320 and consequently primary auditory cortex 150 have been determined using these 3-dimensional MRI image processing techniques, the actual primary auditory cortex 150 can be surgically exposed and prosthetic 200 can be accurately inserted into primary auditory cortex 150. FIG. 4 shows prosthetic 200 just prior to insertion into primary auditory cortex 150. In addition, FIG. 4 shows a speech processor 410 coupled to leads 238 via coupling cable 414. Examples of speech processors for speech processor 410 include Nucleus Device made by Cochlear Corporation. Speech processor 410 can be miniaturized and placed directly above ear 416 in the patient's mastoid. FIG. 4 also shows additional diagnostic equipment including an oscilloscope 420 coupled to prosthetic 200 via cable 424.

Figure 5:
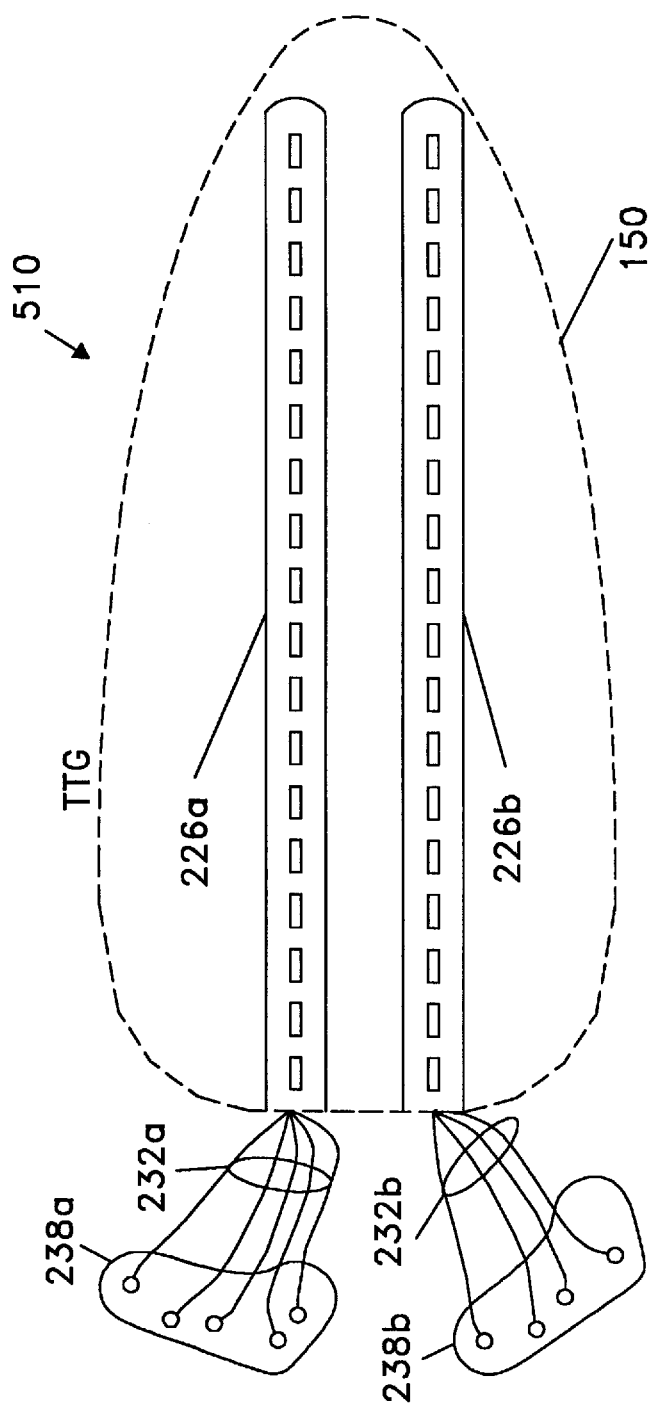
FIG. 5 shows a prosthetic which includes two longitudinal supports according to another embodiment of the invention.

FIG. 5 shows a prosthetic 510 which includes two longitudinal supports 226a and 226b according to another embodiment of the invention. Although two supports are shown, three or more such supports could be used. Longitudinal support 226a has wires 232a with corresponding leads 238a and longitudinal support 226b has wires 232b and leads 238b. Leads 238a and 238b are again connected to speech processor 410 as in FIG. 4. In addition, scope 420 can be used to observe signals output to longitudinal support 226a and 226b.

Figure 6:
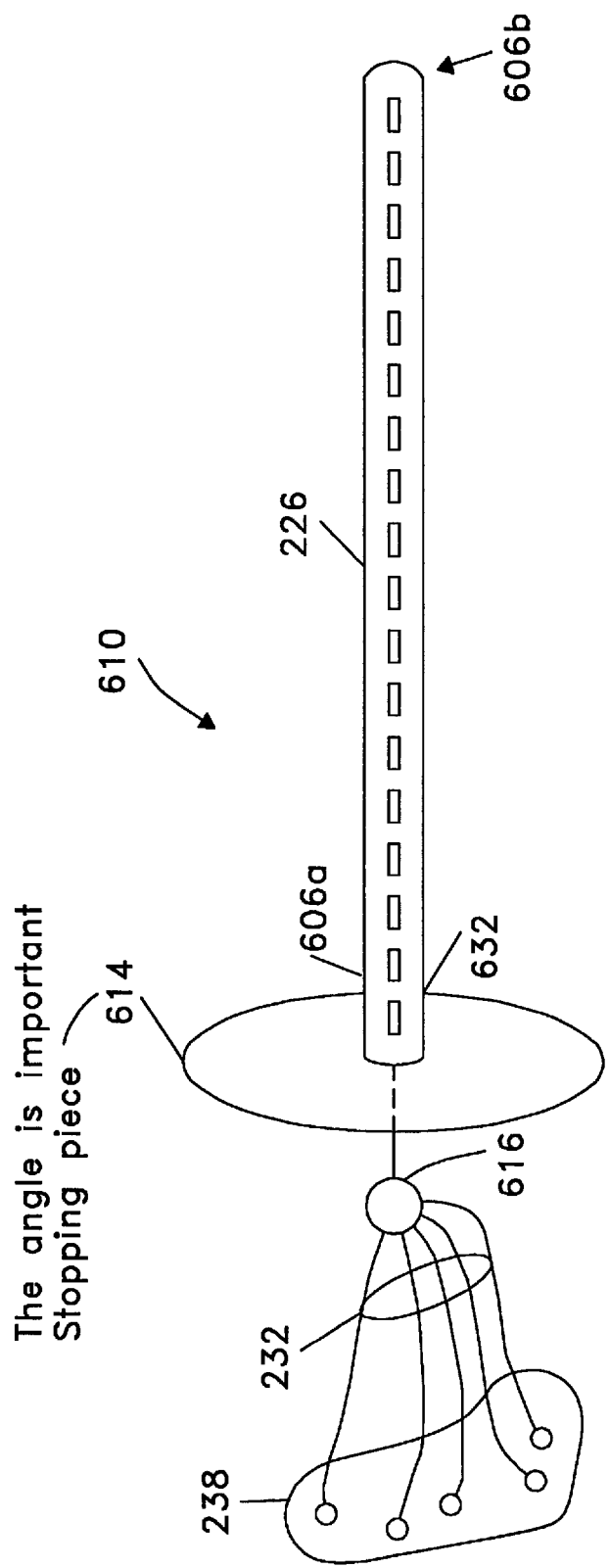
FIG. 6 shows a prosthetic according to yet another embodiment of the invention.

FIG. 6 shows a prosthetic 610 according to yet another embodiment of the invention. In particular, FIG. 6 shows longitudinal support rod 226 with first end 606a and second end 606b. End 606a is arranged in the region of primary auditory cortex 150 with low tones (or high tones as previously discussed) and second end 606b is arranged in the region of primary auditory cortex 150 with high (or low) tones in a manner similar to first end 206a and second end 206b of FIG. 2. Here, however, longitudinal support 226 has a sphere 616 which is stopped by a stopping piece 614. This enables the physician to insert longitudinal support 226 at a wide range of angles and yet secure prosthetic 610 once longitudinal support 226 has been inserted.

Figure 7A:
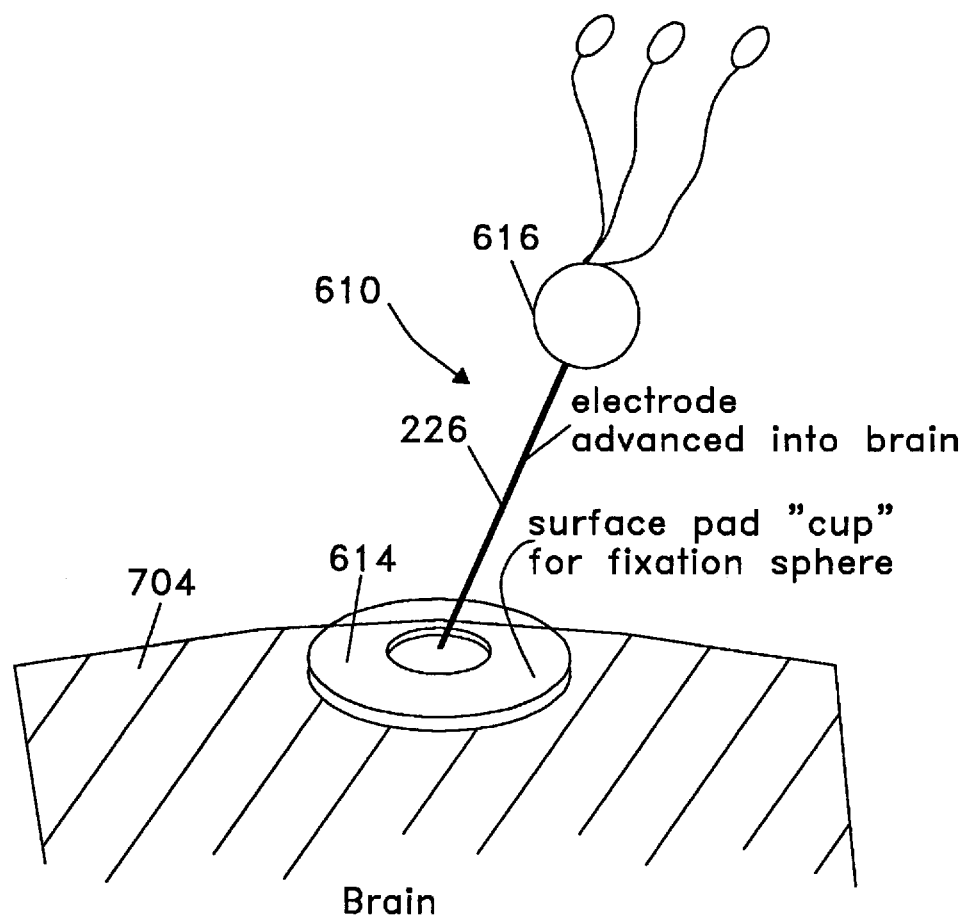
FIG. 7A shows the prosthetic of FIG. 6 as looking down on the patient's brain surface.
Figure 7B:
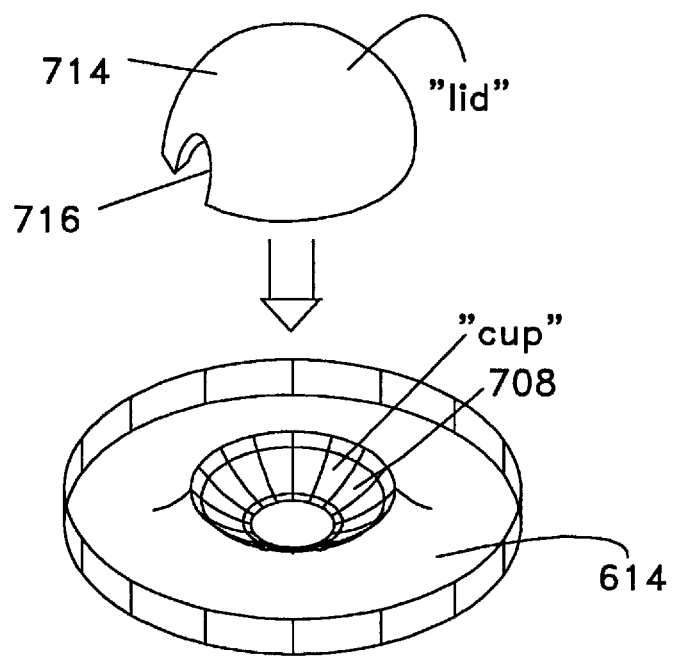
FIG. 7B shows a closer view of a stopping piece with a cup and a lid, and FIG. 7C corresponds to FIG. 7A with the support inserted.
Figure 7C:
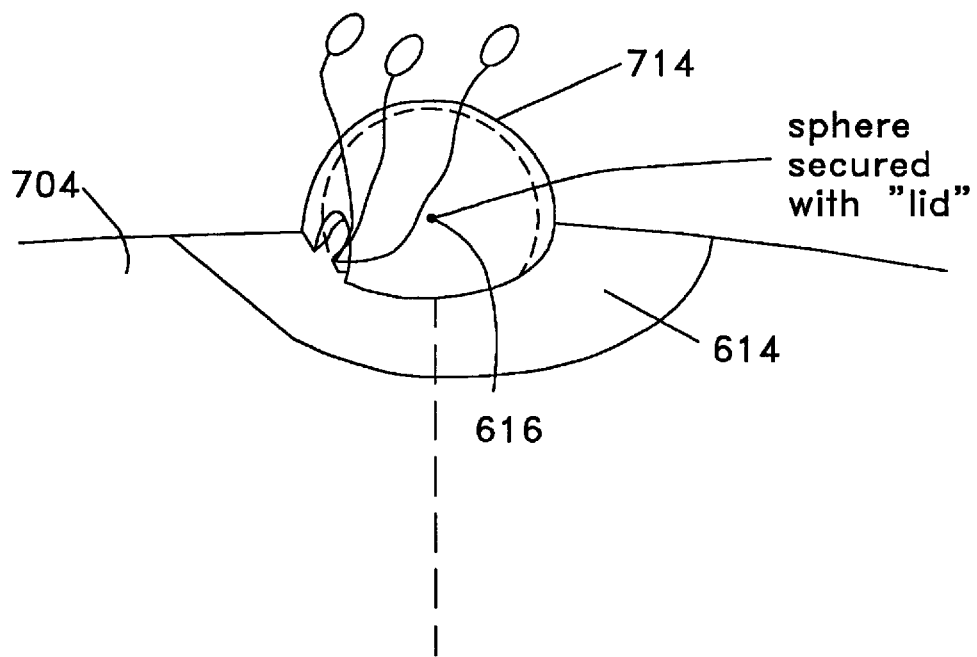

FIG. 7A shows prosthetic 610 of FIG. 6 as looking down on the patient's brain surface 704. FIG. 7B shows a closer view of stopping piece 614 with a cup 708 and a lid 714 with a notch 716 for passing leads 232. FIG. 7C corresponds to FIG. 7A with support 226 inserted into surface 704 and sphere 616 resting in cup 708. FIG. 7C also shows lid 714 covering sphere 616 with leads 232 extending out of notch 716.

Figure 8:
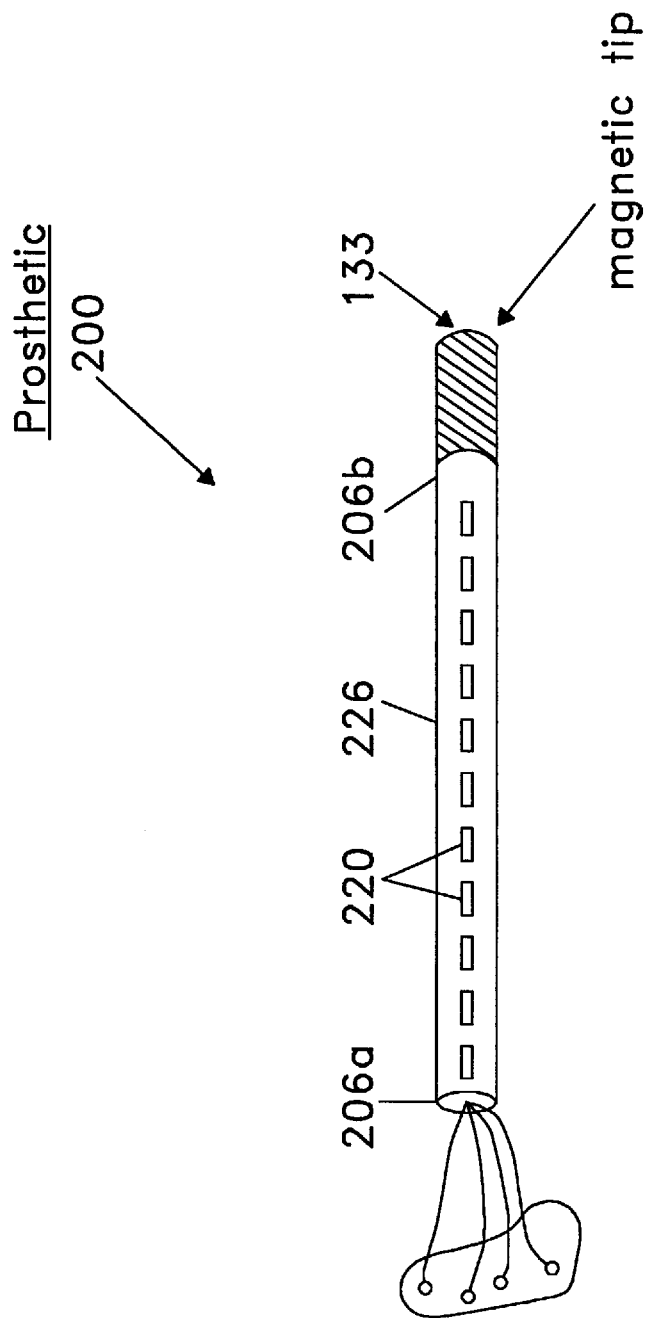
FIG. 8 shows a magnetically tipped multicontact neural prosthesis.

FIG. 8 shows a multicontact electrode apparatus 200 according to another embodiment of the invention, in which longitudinal support 226 is equipped with a magnetic tip 133 at its distal end 206b. The attribute of a magnetic tip allows for the introduction and directed movement of the prosthesis to the target tissue by the application of an external magnetic field, as described herein in connection with the disclosed apparatus for performing magnetic pallidotomy. Furthermore, the precise location of a magnetically tipped neural prosthesis, which has previously been inserted following 3-dimensional MRI imaging and surgical exposure of the auditory cortex, may be fine tuned by the application of a suitable external magnetic field (Gillies, G. T. et al., "Magnetic manipulation instrumentation for medical physics research," *Rev. Sci. Instrum.*, 65:533–562, 1994). In the latter case, the magnitude and direction of the applied magnetic field may be changed in response to the patient's auditory sensations following electrical stimulation of the auditory cortex.

Stereotactic Surgical Electrode Assembly

While all cells maintain an electrical potential across their membranes, nerve cells (neurons) are highly specialized in using membrane potentials (action potentials) to transmit signals from one part of the body to another. The action potential of a neuron represents a transient depolarization of its membrane over a period of a few milliseconds. Action potentials, in turn, have proved to be valuable indicators of the physiological status and functionality of those neurons. For example, in stereotactic pallidotmy the action potential of a neuron is used as the basis for determining whether to make a lesion at the site of the particular neuron.

Monopolar microelectrodes of the prior art comprise stiff wires which are electrically insulated except for a relatively short, sharpened tip. By keeping the length of the uninsulated tip short, an electrode with a high impedance (>1 megaohms) is obtained. A higher impedance microelectrode allows for a more precise measurement of action potentials relative to ground (using such prior art microelectrodes, typically the entire body of the patient is grounded). In contrast, electrodes with a larger area of exposed (uninsulated) surface are characterized by a lower impedance (a few to <1 megaohms). Consequently, larger electrodes with lower impedances ordinarily record voltage transients (field potentials) associated with larger volumes of tissue; but are unable to record action potentials from individual cells.

In accordance with an embodiment of this invention, it has now been discovered that action potentials can be accurately recorded from individual neurons using electrodes with a relatively large exposed surface area, and a relatively low impedance. Namely, action potentials of individual cells can be recorded using a microelectrode comprising a novel multipolar contact array. In a preferred embodiment, each microelectrode comprises a pair of contacts (corresponding to a bipolar contact) in close juxtaposition, which are coupled to at least one differential amplifier (Bak Electronics, Germantown, Md.), and differential recordings are made from one contact relative to the other (instead of relative to patient ground as in the prior art). In another embodiment, each microelectrode may comprise tripolar contact arrays (stereotrodes, B. L. McNaughton, et al., "The stereotrode: a new technique for simultaneous isolation of several single units in the central nervous system from multiple unit recordings," *J. Neurosci. Methods,* 8:391–397, 1983.

Dual purpose electrode assemblies bearing neuron-monitoring electrodes, according to the invention, are useful in carrying out a range of medical procedures. As will be apparent to the skilled artisan, electrode assemblies of the instant invention are particularly useful for performing various stereotactic procedures on the brain. Such stereotactic procedures include various surgical procedures on specific regions of brain tissue, including stereotactic pallidotomy and stereotactic thalamotomy. Electrode assemblies under the invention may also be used for chronically inactivating a previously-monitored, specific region of a patient's brain tissue, without forming a lesion therein. In another embodiment, electrode assemblies of the instant invention are also useful in delivering one or more chemical agents to a previously-monitored, specific region of a patient's tissues. Such chemical agents may be either toxic chemicals (where inactivation of neurons is called for), or therapeutic drugs (where therapy is indicated).

A medical procedure performed on a patient's brain, according to the invention, will now be described in general terms. Following visualization of the target tissue by various imaging procedures well known in the art, a dual purpose electrode assembly 103 bearing at least one neuron-monitoring electrode 135 is introduced into the patient's brain in the vicinity of the target tissue via introducer tube 101, as described herein. The positioning of the various parts of electrode assembly 103, including electrode support shaft 137, may then be fine-tuned as appropriate. Electrode potentials from cells or tissues may then be recorded and the physiological status of the cells or tissues is monitored, over a period of up to several days if necessary. Tissue at the site(s) of the monitored neuron(s) may then be treated. Treatment will vary depending on the patient's overall condition, and/or on the recordings of electrical potentials. For example, treatment may be in the form of reversible or irreversible inactivation of one or more cells or a region of tissue, or by the delivery of one or more therapeutic drugs.

Various embodiments of electrode assembly 103 of the instant invention will now be described, particularly in the context of performing stereotactic pallidotomy. Other applications and uses of said electrode assembly will be apparent to the skilled artisan, and are hereby stated to be within the scope of the invention, as delineated by the claims appended hereto.

Stereotactic Pallidotomy

The globus pallidus is a conical subcortical structure within the brain which is involved in the control of movement. FIG. 12A shows the gross morphology, and relative size of the globus pallidus, as well as its approximate location and orientation within the brain. During recent years, stereotactic pallidotomy has become recognized as a valuable procedure in the treatment of Parkinson's disease (see, for example, Laitinen, L. Y., et al., "Leksell's posteroventral pallidotomy in the treatment of Parkinson's disease," *J. Neurosurg.*, 76:53–61, 1992; Iacono, R. P., et al., "The Results, indications, and physiology of posteroventral pallidotomy for patients with Parkinson's disease," *Neurosurgery*, 36:1118–1127, 1995; and references cited therein). Simply stated, the rationale for the success of this treatment is as follows. Parkinson's disease causes dysfunction due to loss of dopaminergic innervation in a part of the movement control circuit (Putamen and Caudate) distinct from the globus pallidus. However, because of the nature of the circuit, the dysfunction in Parkinson's disease can be ameliorated by disruption of the circuit at the point of the globus pallidus (see, for example, Laitinen, L. Y., et al., "Leksell's posteroventral pallidotomy in the treatment of Parkinson's disease," *J. Neurosurg.*, 76:53–61, 1992; Iacono, R. P., et al., "The results, indications, and physiology of posteroventral pallidotomy for patients with Parkinson's disease," Neurosurgery, 36:1118–1127, 1995; and references cited therein.)

Figure 12C:
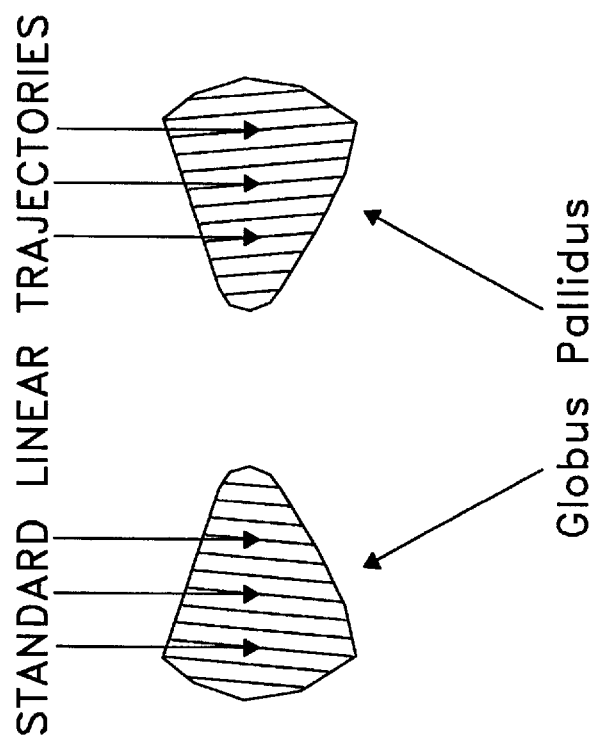
FIG. 12C shows the parallel linear trajectories of electrode assemblies, according to prior art pallidotomy.

FIG. 12C shows the parallel linear trajectories of electrode assemblies according to prior art pallidotomy. As shown, stereotactic pallidotomy techniques of the prior art have relied on the sequential insertion of first a microelectrode to monitor the physiologic response of neurons within a defined region of the globus pallidus, and, if the response calls for inactivation (lesioning) of neurons in that region, a second, larger, lesion-producing macroelectrode, or a cryogenic device, is targeted to the same site for the purpose of producing a lesion thereat. This process is repeated until a suitable number of sites within the globus pallidus have been monitored and, if appropriate, the neuron(s) at that site inactivated. A further feature of prior art pallidotomy is that the trajectories of the electrodes are perpendicular to the long axis of the globus pallidus (see for example FIG. 12C) Therefore, the prior art pallidotomy process outlined in the Background of the Invention section of this specification requires the surgeon to make several passes through normal brain tissues during the operation, with a concomitant risk of brain damage.

The instant invention is concerned with an apparatus comprising an electrode assembly including an electrode support shaft, in which electrode assembly 103 and electrode support shaft 137 are broadly equivalent to the multicontact prosthesis 200 and longitudinal electrode support 226, respectively, of the neural prosthesis described above. Differences between the recited parts of the respective devices will be readily apparent to the skilled artisan from their descriptions herein.

Electrode assembly 103 and electrode support shaft 137 of the instant invention may be either rigid or flexible. In a preferred embodiment, both electrode assembly 103 and electrode support shaft 137 are flexible. In one embodiment electrode support shaft 103 of the instant invention bears at least one neuron-monitoring electrode 135A/135B. In a preferred embodiment electrode support shaft 103 of the instant invention bears at least one bipolar neuron-monitoring microelectrode 135A. Preferably electrode support shaft 137 comprises an outer sheath 143 constructed of a flexible polymeric or co-polymeric material. A particularly preferred sheath material comprises tecoflex-polyurethane (Thermetics, Woburn, Mass.). Preferably electrode support shaft 137 bears a plurality of bipolar neuron-monitoring microelectrodes 135A, each bipolar microelectrode 135A comprising two electrical contacts 136, in the form of a pair of fine wires lying external to, and approximately parallel with, the external sheath of the shaft. Each electrical contact 136 is coupled to an electrical lead 129 comprising at least one strand of electrically conductive material, whereby a suitable electric current may be conducted to or from each of said electrical contacts 136. Preferably each electrical lead 129 comprises a flexible wire coated with an electrically insulating material. More preferably each strand of electrically conductive material comprises platinum and iridium, and has a diameter in the range of 10–200 micrometers, more preferably in the range of 20–100 micrometers and most preferably in the range of 30–70 micrometers. In a preferred embodiment the electrically insulating material coating each electrical lead comprises polytetrafluoroethene (Teflon®). In another embodiment electrode support shaft 137 of electrode assembly 103 is flexible, bears a plurality of bipolar neuron-monitoring microelectrodes 135A, and is equipped with a magnetic tip 133 at its distal end. Magnetic tip 133 of the electrode support shaft 137 is responsive to an external magnetic field, thereby allowing for its maneuverability in response to controlled changes in an applied magnetic field. The magnetic manipulation of medical devices within a patient's body, in general, including magnetic stereotactic procedures, is known in the art (see, for example Grady, M. S., et al., "Magnetic stereotaxis: a technique to deliver stereotaxic hypothermia," *Neurosurg.*, 27:1010–1016, 1990; Grady, M. S., et al., "Nonlinear magnetic stereotaxis: Three dimensional, in vivo remote magnetic manipulation of a small object in canine brain," *Med. Phys.*, 17:405–415, 1990; Gillies, G. T., et al., "Magnetic manipulation instrumentation for medical physics Research," *Rev. Sci. Instrum.*, 65:533–562, 1994, and references cited therein.

In one embodiment of the invention, each bipolar microelectrode 135A is in the form of a pair of fine wires closely juxtaposed on electrode support shaft 137, and is capable of monitoring the activity of an individual neuron or cell by outputting electrical signals indicative of the physiological status of the particular neuron or cell. The physiological status of a neuron or cell may be used to determine whether to inactivate that particular region of the brain.

Under the invention, neurons targeted for inactivation may be inactivated by a variety of different mechanisms and for various time periods. For example, neurons may be inactivated by exposure to radiation, infusion of a toxic chemical, cryogenic treatment (cooling), or prolonged electrical stimulation. A toxic chemical, under the invention, may be a chemical known to be a neurotoxin or a broad spectrum cytotoxin. Cryogenic treatment may be administered from at least one miniaturized cryogenic device located at one or more specific sites on the electrode support shaft. A preferred mechanism for inactivating neurons is by exposure to radio frequency (RF) radiation, using, for example, a RF lesion generator system such as model RFG-3C manufactured by Radionics (Burlington, Mass.). These examples should not be considered to limit the invention as defined by the claims in any way.

Inactivation of neurons may be reversible or irreversible. In general, inactivation of neurons resulting from cooling or electrical stimulation is, to some extent, reversible; whereas neuron inactivation by exposure to radiation or infiltration of a toxic chemical normally results in a permanent lesion and is irreversible.

In a preferred embodiment, electrode support shaft 137 is flexible, is equipped with a magnetic tip 133 responsive to an applied external magnetic field, and bears a plurality of neuron-monitoring microelectrodes 135A and a plurality of neuron-inactivating sites positioned along electrode support shaft 137. In a more preferred embodiment, electrode support shaft 137 is flexible, is equipped with a magnetic tip 133 responsive to an applied external magnetic field, and bears a plurality of bipolar neuron-monitoring microelectrodes 135A and an equal number of neuron-inactivating sites positioned along electrode support shaft 137, wherein each of said plurality of bipolar neuron-monitoring microelectrodes 135A is positioned, along the longitudinal axis of electrode support shaft 137, coincidental with one of said neuron-inactivating sites. Each neuron-inactivating site is capable of inactivating one or more neurons located adjacent to that site. A plurality of bipolar neuron-monitoring microelectrodes 135A may be located at different points on the circumference of electrode support shaft 137, in other words, the position of the microelectrodes may be offset with respect to the long axis of the electrode support shaft. In another embodiment of the dual purpose electrode support shaft 137, a plurality of bipolar neuron-monitoring microelectrodes 135A may be located at different points on the circumference of electrode support shaft 137 but at the same longitudinal position on the support shaft. For example, two bipolar neuron-monitoring microelectrodes 135A may be diametrically opposed, as shown in FIG. 11B. This latter arrangement allows for the simultaneous recording of two action potentials, one from each side of the support shaft.

In one embodiment of the invention, each neuron-inactivating site on electrode support shaft 137 is in the form of a delivery port 141 for releasing a lesion-producing toxic chemical. Each delivery port 141 may be activated to release a measured dose of a toxin to the neuron(s), cell(s), or tissue targeted for inactivation, thereby inducing a localized lesion thereat. Many cytotoxic chemicals are known in the art, and may be used either alone (unconjugated), or conjugated to a specific monoclonal antibody or other carrier molecule (see, for example Stan, A. C., et al., "In vivo inhibition of angiogenesis and growth of the human U-87 malignant glial tumor by treatment with an antibody against basic fibroblastic growth factor," J. Neurosurg., 82:1044–1052, 1995). One example of a cytotoxic chemical is ibotenic acid which selectively destroys cell bodies without damaging fibers of passage (Guldin, W. O. & Markowitsch, H. J., "No detectable remote lesions following massive intrastriatal injections of ibotenic acid," Brain Res., 225:446–451, 1992.

In another embodiment of the invention, each neuron-inactivating site on electrode support shaft 137 is in the form of a macroscopic stimulating electrode capable of chronic electrical stimulation of the neuron(s), cell(s), or tissue targeted for inactivation, thereby inducing localized, transient neuron dysfunction. With this type of treatment neuron function is generally regained some time after cessation of electrical stimulation.

In a further embodiment of the invention, each neuron-inactivating site on electrode support shaft 137 is in the form of a cryogenic device, i.e. an element which causes localized cooling of those neurons or tissues with which it is in physical contact. Generally, neuron inactivation resulting from cooling is reversible, and neuron function is restored after a period of time following cessation of treatment.

In another embodiment of the invention, each neuron-inactivating site on electrode support shaft 137 is in the form of a lesion-producing macroelectrode 139, which when energized delivers radio frequency (RF) energy to the neuron(s), cell(s), or tissue targeted for inactivation, thereby inducing a localized lesion thereat.

Although neuron inactivation is described herein primarily with reference to lesion production via macroelectrodes 139, this should not be considered as limiting the scope of the invention in any way.

A flexible embodiment of electrode assembly 103 can be initially introduced into the vicinity of the target tissue, such as the globus pallidus, via introducer tube 101 that has previously been stereotactically inserted into the patient's brain. Introducer tube 101 of the instant magnetic pallidotomy device is equivalent to the introducer described above in connection with neural prosthesis 200. Once inserted in the patient's brain, the magnetic tip 133 of electrode assembly 103 may be urged forwards by the application of an external magnetic field of suitable magnitude and direction. By changing the magnitude and direction of the magnetic field electrode support shaft 137 can be directed forwards to varying extent and in different directions so that it occupies the desired conformation within the target tissue. In this situation, electrode support shaft 137 can be said to be "draped" within the target tissue. Preferably the magnetic field is generated by an electromagnet or multi-coil electromagnet system positioned adjacent to, or surrounding, the head or other appropriate body part of the patient. The electromagnet or multi-coil electromagnet system may be attached to a robotic arm. One or more computers may be used to control movement of the robotic arm, and the magnitude and direction of the magnetic field, as well as to visualize the location and movement of the magnetic device within the patient.

The manipulation of magnetic medical devices within the body by the application of a magnetic field is described more fully in U.S. Pat. No. 4,869,247 and U.S. Pat. No. 5,125,888 both of which are incorporated by reference herein in their entirety. Reference is also made to the following publications: Howard III, M. A., et al., "Magnetic movement of a brain thermoreceptor," Neurosurgery, 24:444–448, 1989; Grady, M. S., et al., "Magnetic stereotaxis: a technique to deliver stereotaxic hypothermia," Neurosurg., 27:1010–1016, 1990; Grady, M. S., et al., "Nonlinear magnetic stereotaxis: Three dimensional, in vivo remote magnetic manipulation of a small object in canine brain," Med. Phys., 17:405–415, 1990; Gillies, G. T., et al., "Magnetic manipulation instrumentation for medical physics Research," Rev. Sci. Instrum., 65:533–562, 1994, and references cited therein.

Once the neurons adjacent to neuron-monitoring electrodes 135A/135B and macroelectrodes 139 have been monitored and subsequently inactivated, if appropriate, electrode assembly 103 may be withdrawn to a home position within introducer tube 101 by exerting a pulling force on tether line 127. Electrode support shaft 137 may then be reintroduced into the patient and repositioned within the patient's tissues, for example, to sample additional regions within the globus pallidus. As electrode assembly 103 is reintroduced into the patient, tether line 127 retracts but its proximal end is retained within the end piece 113 of introducer tube 101 by anchor plate 125 which is fixedly attached to the proximal end of tether line 127.

Referring now to the drawings, in which like reference numerals designate like or corresponding elements throughout, there is shown in FIGS. 9–11, 13–17, 20 and 23 various elements, components or embodiments of an apparatus for introducing the distal end of at least one electrode assembly 103 into the tissues of a patient. FIGS. 9A, 9B and 9C illustrate three different embodiments of an electrode support shaft, in which support shaft 137 may be rigid (as depicted in FIGS. 9A and 9B) or flexible (as shown in FIG.

Figures 9A, 9B, 9C:
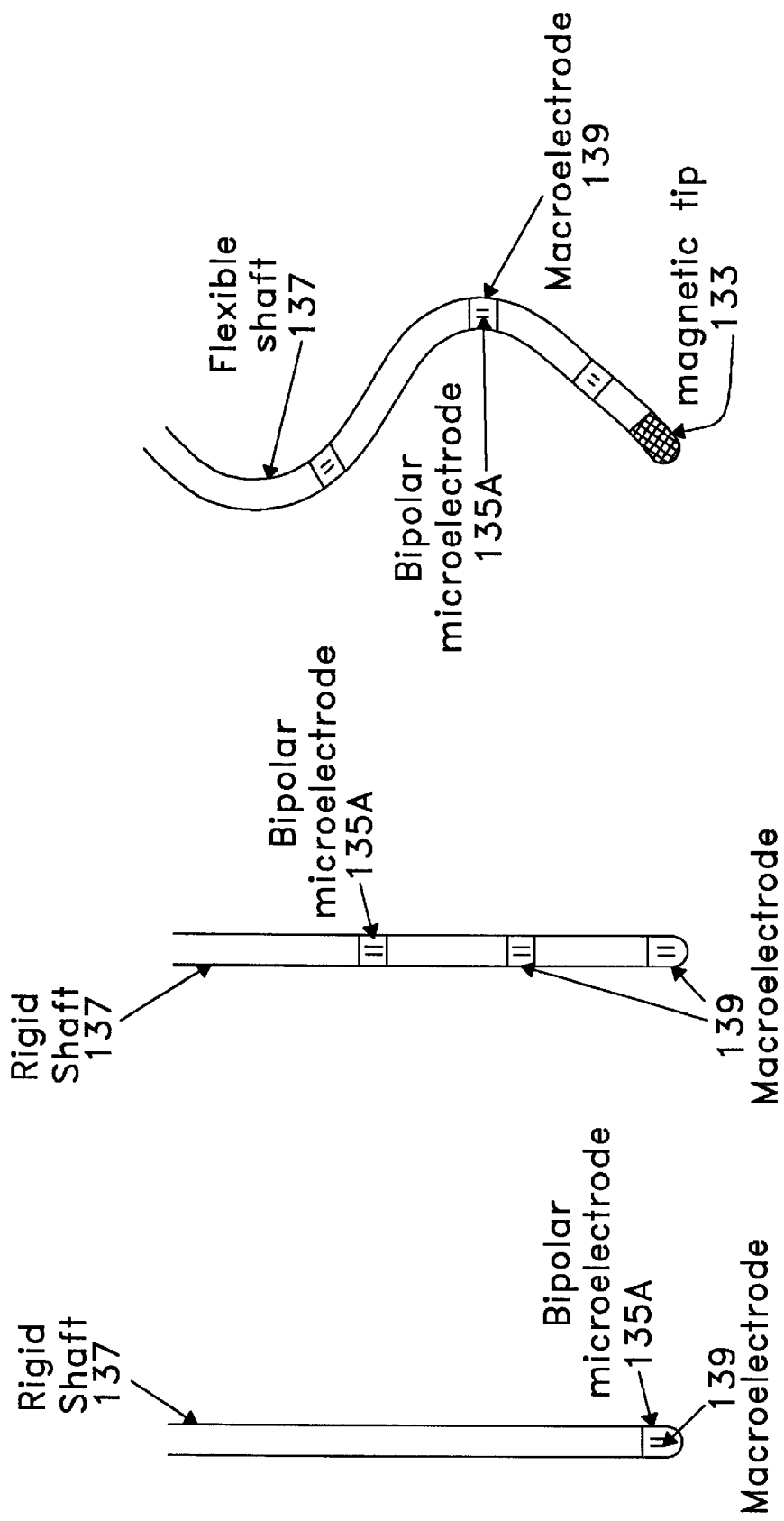
FIGS. 9A, 9B and 9C illustrate three different embodiments of an electrode support shaft.

9C). Preferably support shaft 137 bears ar least one bipolar neuron-monitoring microelectrode 135A and at least one macroelectrode 139. Support shaft 137 may have additionally magnetic tip 133 as shown in FIG. 9C.

Figure 10:
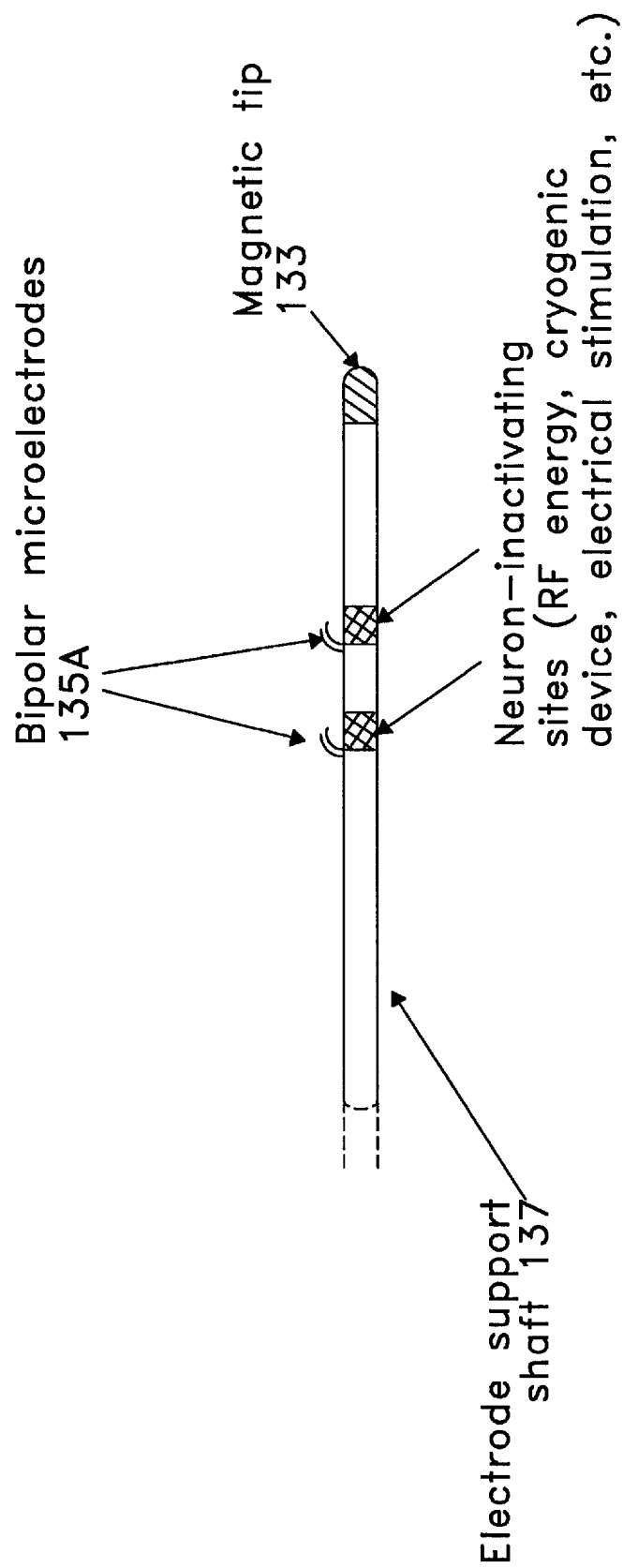
FIG. 10 shows an electrode support shaft bearing a plurality of bipolar neuron-monitoring microelectrode positioned adjacent to a plurality of neuron-inactivating sites.

FIG. 10 shows an electrode support shaft 137 having a magnetic tip 133 and bearing a plurality of bipolar neuron-monitoring microelectrodes 135A. Positioned adjacent to each neuron monitoring microelectrode 135A is a neuron-inactivating site.

FIGS. 11A and 11B show details of parts of an embodiment of an electrode support shaft 137 of a dual purpose electrode assembly 103, bearing bipolar neuron-monitoring microelectrodes 135A, in which the pair of electrical contacts 136 of microelectrodes 135A are closely juxtaposed, and are positioned coincidental with, and external to, macroelectrode 139.

Figure 13A:
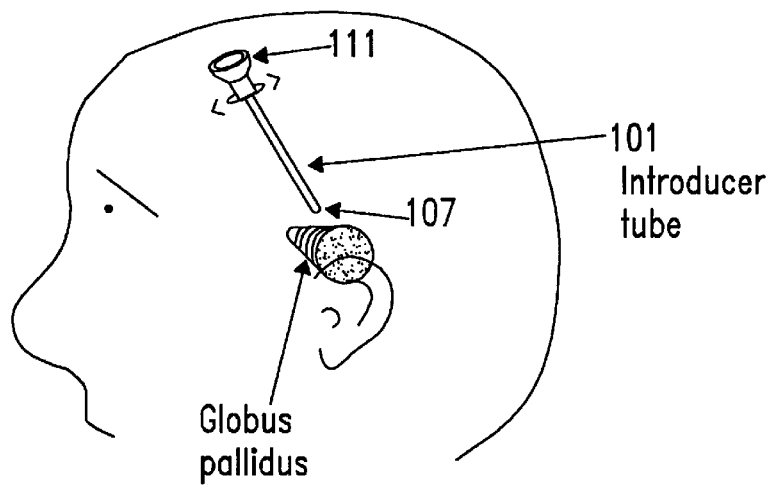
FIG. 13A–13C show apparatus for performing magnetic stereotactic surgery.
Figure 13B:
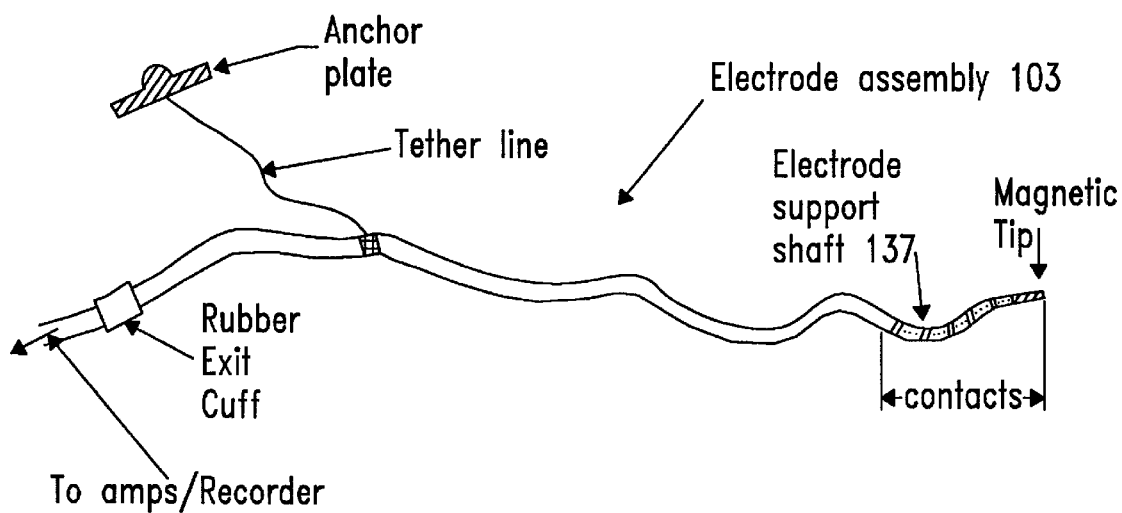
Figure 13C:
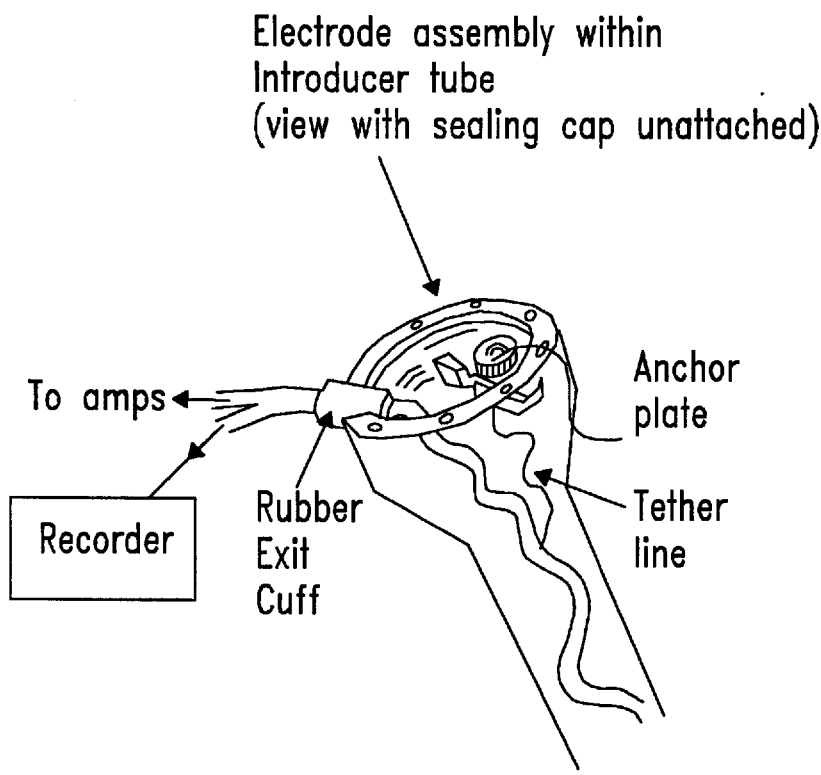

FIGS. 13A–13C show apparatus for performing magnetic stereotactic surgery. FIG. 13A shows introducer tube 101 positioned within the patient's skull. Electrode assembly 103 is passed through introducer tube 103 towards the targeted tissue. FIG. 13B shows the electrode assembly 103 ex situ. Electrode assembly 103 comprises tether line 127, anchor plate 125, electrical leads 129 gathered at rubber exit cuff 131, and at its distal end, electrode support shaft 137. FIG. 13C shows electrode assembly 103 housed within introducer tube 101 with sealing cap 119 unattached.

Figure 14:
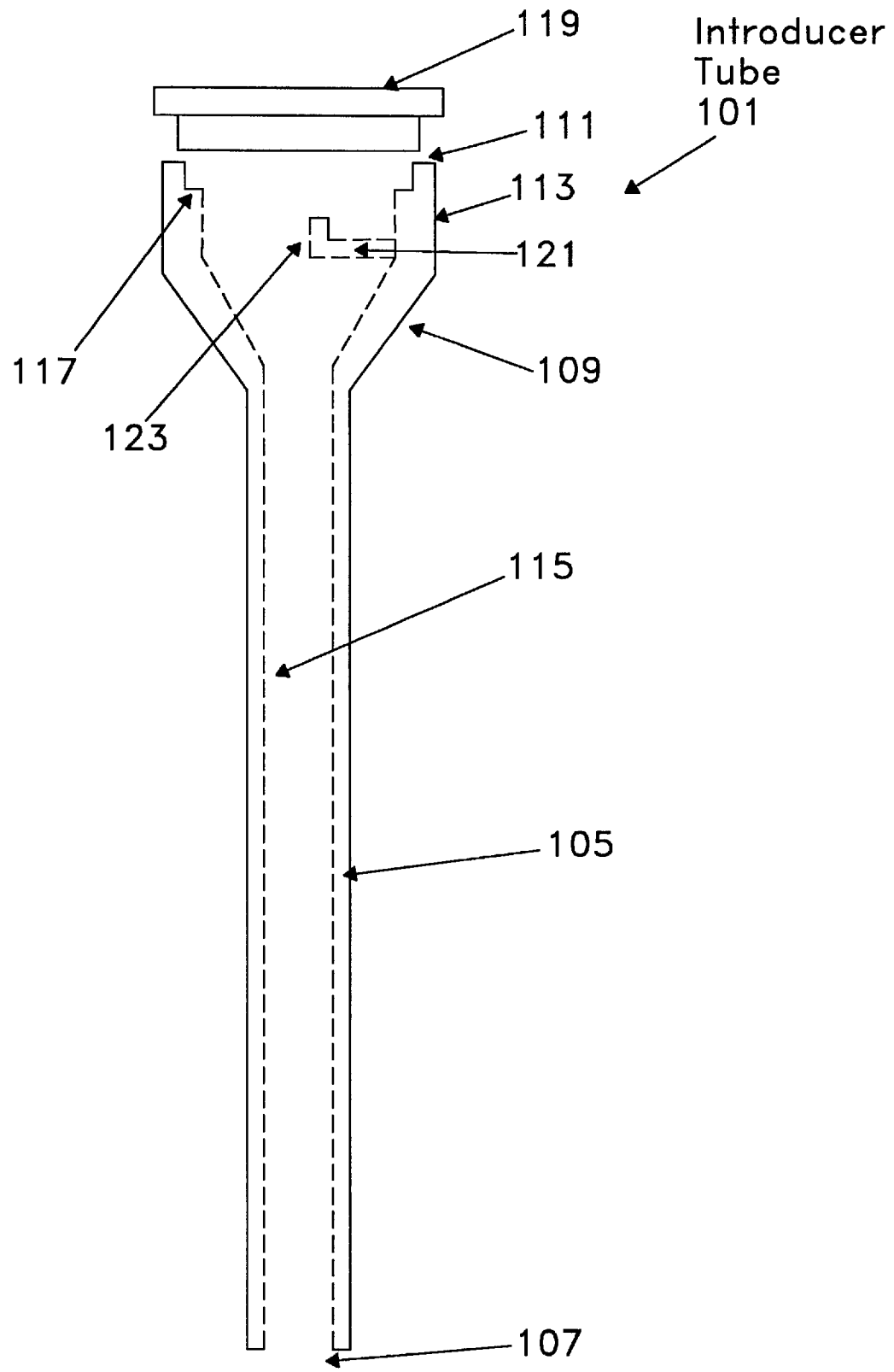
FIG. 14 shows a general view of the introducer tube in cross section.

FIG. 14 shows a general cross sectional view of introducer tube 101. Introducer tube 101, may be flexible or rigid in its construction, and includes elongate cylindrical portion 105 with an open distal end 107, conical neck portion 109 which is continuous with portion 105, and at the proximal end 111 of introducer tube 101 is located a short cylindrical end piece 113 continuous with neck portion 109.

In a preferred embodiment the inner wall 115 of introducer tube 101 may be coated with a physiologically acceptable fluid, prior to the introduction of electrode assembly 103, in order to serve as a lubricant and to reduce drag on electrode assembly 103 as it travels within introducer tube 101.

Figure 15:
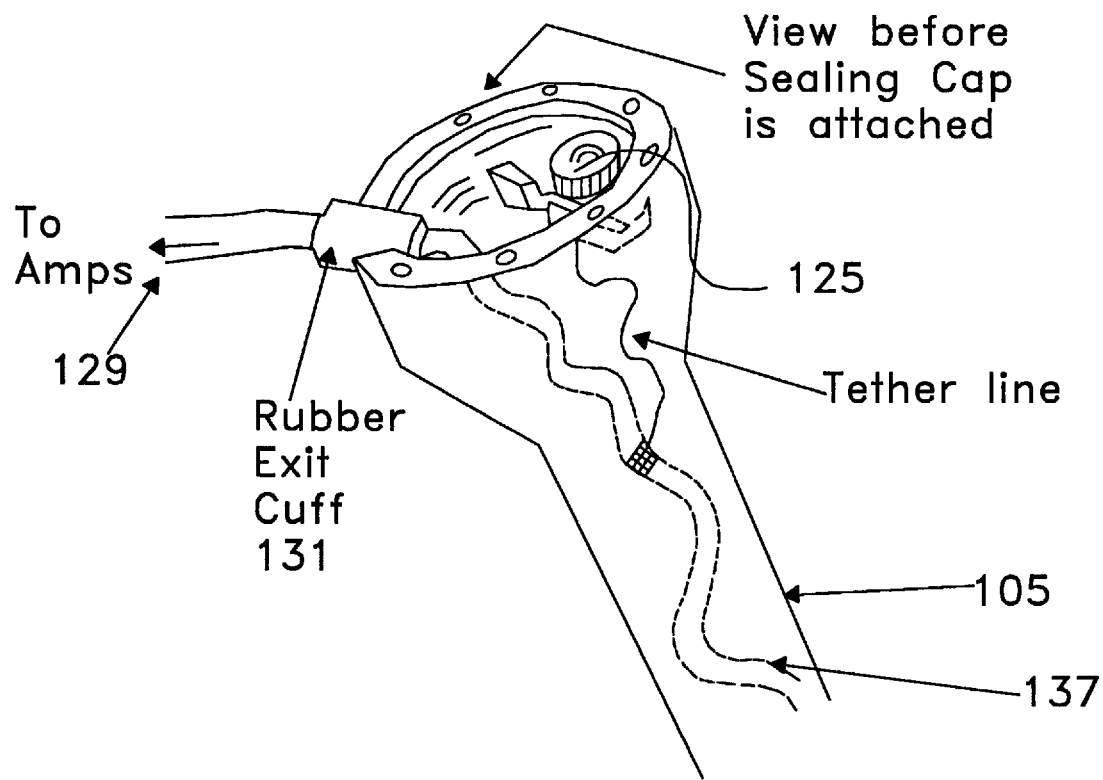
FIG. 15 shows a more detailed view of the proximal end of the introducer tube with the electrode assembly positioned therein, and the sealing cap unattached.

FIG. 15 shows a more detailed view of the proximal end of introducer tube 101 showing electrode assembly 103 positioned substantially within introducer tube 101, and with sealing cap 119 (not shown) unattached. From this position, electrode support shaft 137 may be moved from introducer tube 101 to target tissues and returned to introducer tube 101.

Figure 16:
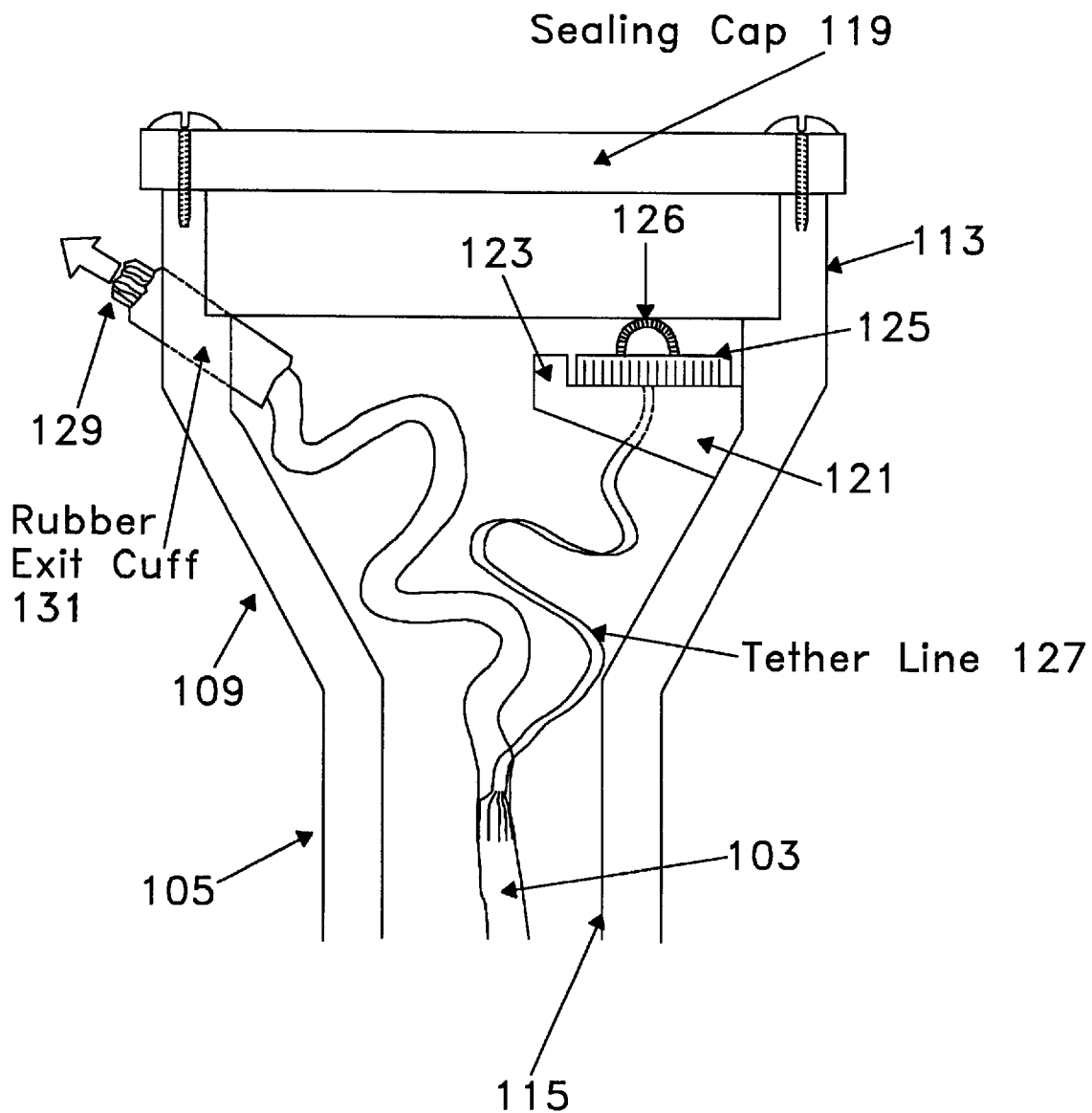
FIG. 16 shows a more detailed view of the proximal end of the introducer tube with the sealing cap attached.

FIG. 16 shows a more detailed view of the proximal end or neck portion 109 of introducer tube 101 with sealing cap 119 attached, in which the inner wall 115 of end piece 113 has a seat 117 to accommodate sealing cap 119. Docking platform 121 is rigidly attached to the inner wall 115 of introducer tube 101. Docking platform 121 includes a perpendicular retaining wall 123 located at the perimeter of platform 121. Anchor plate 125 attached to tether line 127 is retained on docking platform 121 before and during insertion of electrode support shaft 137 into the target tissue. However, to return electrode assembly 103 from the patient to introducer tube 101, anchor plate 125 may be grasped with forceps via the handle 126 of anchor plate 125, and an upward force may then be applied to tether line 127.

Docking platform 121 may be located at different positions along the longitudinal axis of introducer tube 101 within the neck portion 109, provided that the handle 126 of anchor plate 125 is accessible to the surgeon and there is provided sufficient clearance for sealing cap 119 to be seated in the fully closed position.

Electrical leads 129, having rubber exit cuff 131, exit introducer tube 101 in the region of end piece 113 approximately diametrically opposite the location of docking platform 121.

Figure 17:
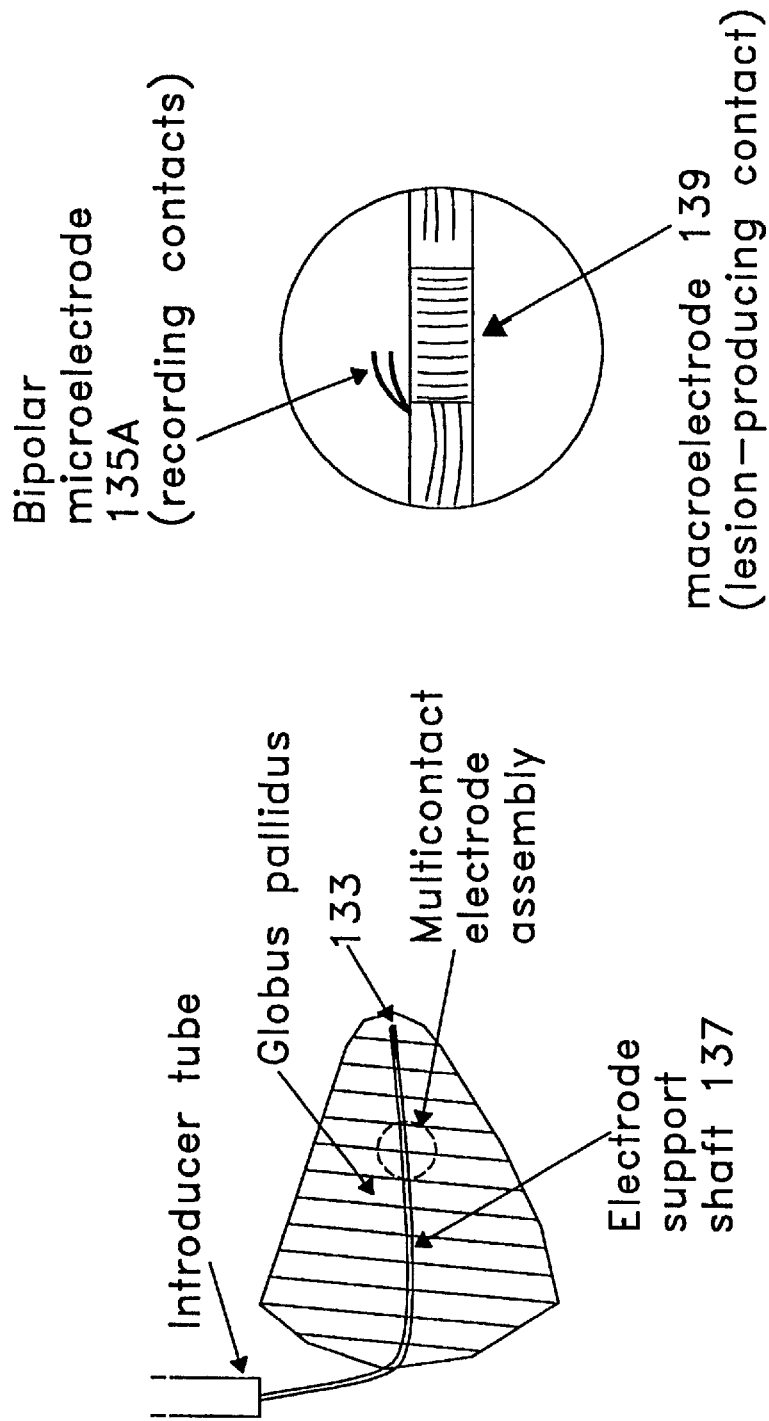
FIG. 17 shows the electrode support shaft positioned within the globus pallidus, together with a magnified view of a microelectrode and a macroelectrode.

FIG. 17 depicts a part of the distal end of an electrode assembly 103 according to a preferred embodiment of the invention, in which electrode support shaft 137 is positioned within the globus pallidus. Electrode assembly 103 has a magnetic tip 133 located at the distal end of electrode support shaft 137, and a plurality of bipolar neuron-monitoring microelectrodes 135A positioned along the long axis of electrode support shaft 137. Each bipolar neuron-monitoring microelectrode 135A is capable of monitoring the physiologic activity of an individual neuron by sensing electrical signals and outputting the sensed signals to a suitable recording means. Preferably, each bipolar neuron-monitoring microelectrode 135A is constructed of a pair of closely juxtaposed electrical contacts 136. Each electrical contact comprises a fine wire having a diameter in the range of 5 to 200 micrometers, more preferably in the range of 5 to 100 micrometers, and most preferably in the range of 10 to 40 micrometers. Adjacent to each bipolar neuron-monitoring microelectrode 135A is located a corresponding, spatially paired, lesion-producing macroelectrode 139. Preferably, the fine wires comprising electrical contacts 136 of bipolar microelelectrodes 135A are sufficiently flexible to "flow" with each pulsation of the brain tissue, and thereby avoid disturbances in the surrounding tissues. In contrast, monopolar neuron-monitoring microelectrodes of the prior art are shorter and stiffer than those of the instant invention, which result in disruption of surrounding tissues and consequently must be removed within a relatively short period of time. The flexible, non-disrupting nature of bipolar microelectrodes 135A as described herein allows them to remain in situ for an extended period of time, thereby enabling the accumulation of more meaningful information on the physiological status of the particular neurons being monitored. Such information is critical in defining exactly where neuron inactivation should be performed; this, in turn, leads to maximum efficacy in the treatment and minimum complications for the patient.

According to a preferred embodiment of the invention, a magnetically tipped dual purpose multicontact electrode assembly 103 is inserted into introducer tube 101, and electrode assembly 103 is anchored to the inner wall 115 of introducer tube 101 via tether line 127 and anchor plate 125. The outside diameter of the electrode support shaft 137, including magnetic tip 133, is in the range of 1 to 4 mm, which is in the range of currently used standard stereotaxic biopsy tools. There is sufficient excess length or slack in electrode assembly 103 and in the attached electrical leads 129 and tether line 127 so that the electrode-bearing region of electrode assembly 103 can be pulled out of introducer tube 101 into the target tissue by a suitably applied external magnetic field. Under computer control, the magnetic tip 133 of electrode assembly 103 is driven into the target tissue along a preselected trajectory.

Figure 18:
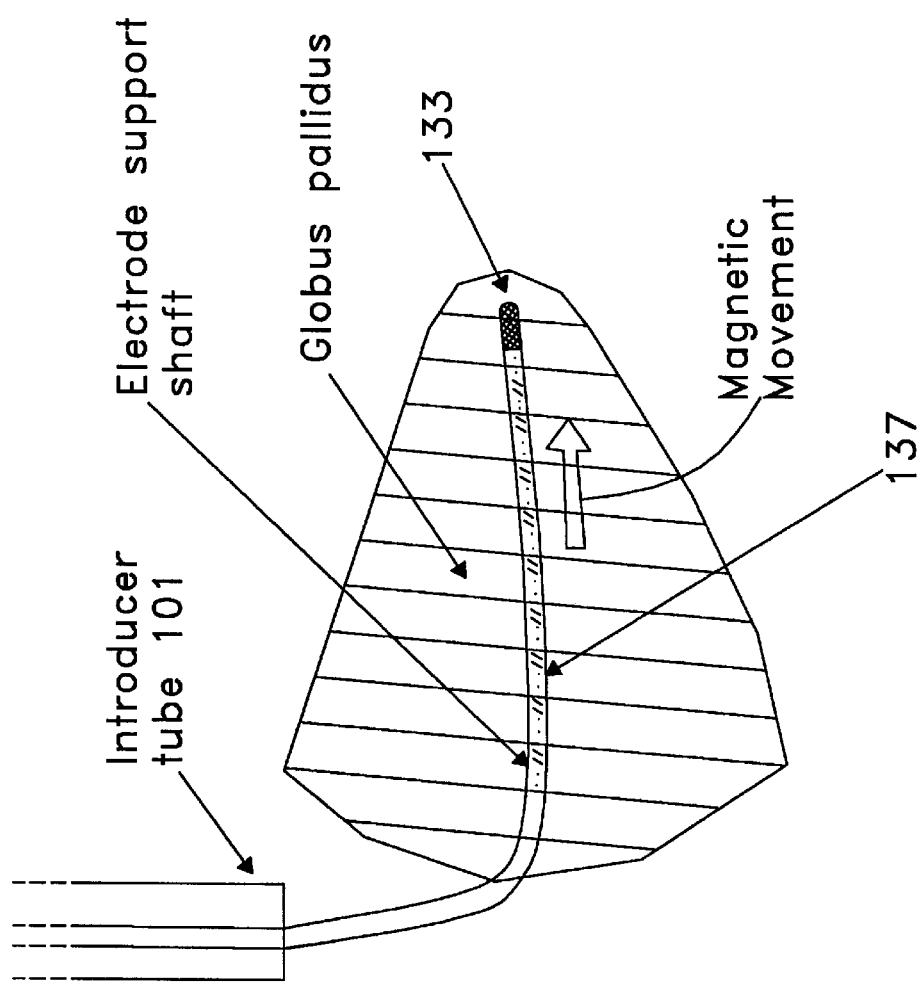
FIG. 18 depicts the movement of the magnetically tipped electrode assembly in the direction away from the introducer tube towards the apex of the globus pallidus.
Figure 19A:
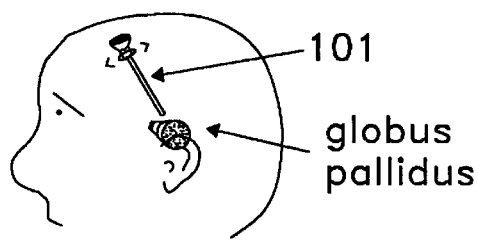
FIG. 19 shows steps in performing magnetic pallidotomy using a dual purpose multicontact electrode assembly.
Figure 19B:
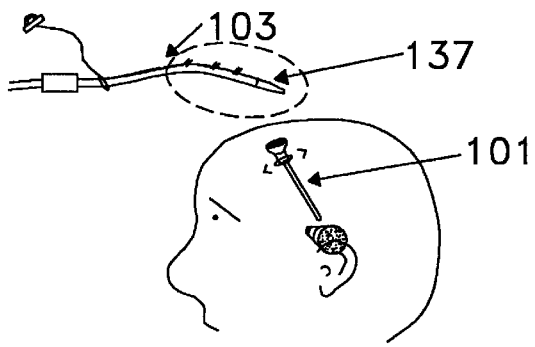
Figure 19G:
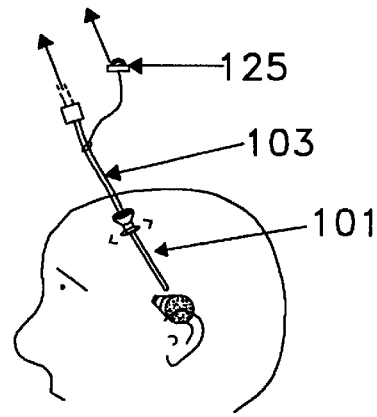
Figure 19C:
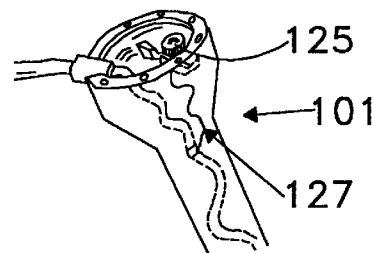
Figure 19D:
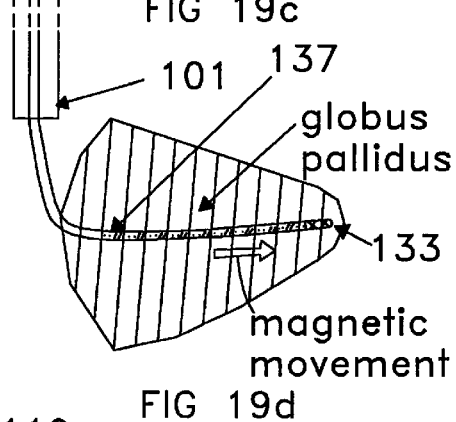
Figure 19F:
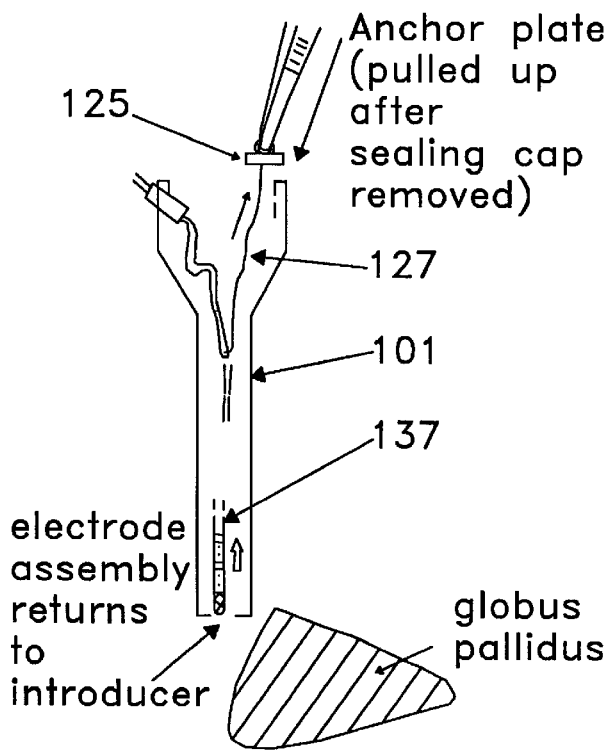
Figure 19E:
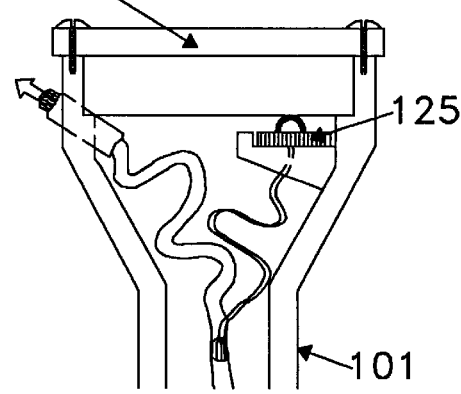

FIG. 18 depicts the movement of a magnetically tipped electrode assembly 103 in the direction away from introducer tube 101 towards the apex of the globus pallidus. The magnetic tip 133 is directed along the selected trajectory by appropriate changes in the magnitude and direction of an applied external magnetic field.

FIG. 19 shows steps in performing magnetic pallidotomy using a dual purpose multicontact electrode assembly 103, in which introducer tube 101 is first inserted into the patient's skull in step a), electrode assembly 103 is introduced into introducer tube 101 in step b), electrode assembly 103 is located in the "home" position within introducer tube 101 in step c), electrode support shaft 137 of electrode assembly 103 is directed into the globus pallidus by magnetic movement in step d), sealing cap 119 is placed on end piece 113 of introducer tube 101 in step e), electrode support shaft 137 of electrode assembly 103 is returned to the "home" position within introducer tube 101 in step f), and electrode assembly 103 is removed from the patient in step g). In the case of the globus pallidus, the preferred trajectory for movement of electrode support shaft 137 generally runs along its entire longitudinal axis, and movement of the magnetic tip 133 to the end of the selected trajectory should take about 20 minutes. Sealing cap 119 can then be attached to the end piece 113 of introducer tube 101, thereby sealing introducer tube 101 at its proximal end 111.

The patient may now be removed from the magnetic surgery suite and returned to the hospital ward. A number of globus pallidus neurons may now be monitored for their physiologic activity, and the activity monitored by each microelectrode 135 may be recorded using a suitable recording device. Based on the neuronal activity monitored and on physiologic criteria, a decision can be made whether to inactivate the particular neuron(s) under study.

If inactivation of a particular neuron is called for, a lesion may be made by energizing the appropriate lesion-producing macroelectrode(s) 139 with a suitable electric current. Preferably, the energy used to produce lesions is in the radio frequency (RF) range. The functional consequences of neuron inactivation can then be assessed by testing the patient on the hospital ward. If the results are satisfactory, the electrode assembly 103 may be removed. Alternatively, it may be desirable to monitor other neurons which are located at different regions within the globus pallidus. In the latter case sealing cap 119 is first removed from introducer tube 101.

Figure 20:
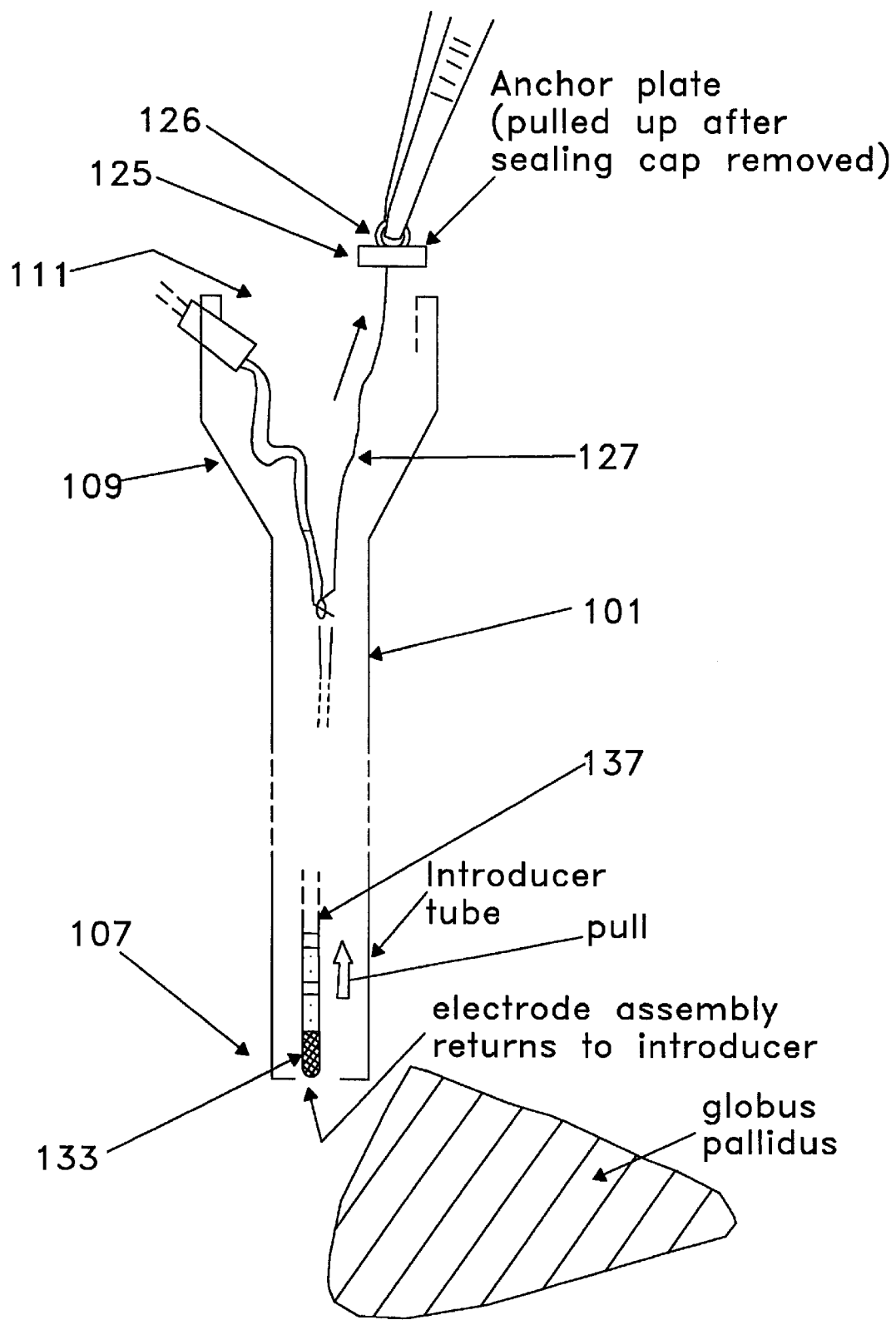
FIG. 20 depicts the tether line of the electrode assembly being pulled upwards and the electrode assembly returning to the introducer tube from the globus pallidus.

As depicted in FIG. 20, the handle 126 of anchor plate 125 may be grasped with forceps and an upward force exerted on tether line 127, whereby electrode assembly 103 is "reloaded" or returned to the home position within introducer tube 101. The magnetic tip 133 of electrode assembly 103 may now be redirected, again by the application of a suitable external magnetic field, along a second preselected trajectory until it once again occupies the desired conformation within the target tissue. The process of monitoring and selectively inactivating individual neurons may then be repeated. A method for performing pallidotomy according to one embodiment of the instant invention is illustrated by way of Example 1.

Figure 21:
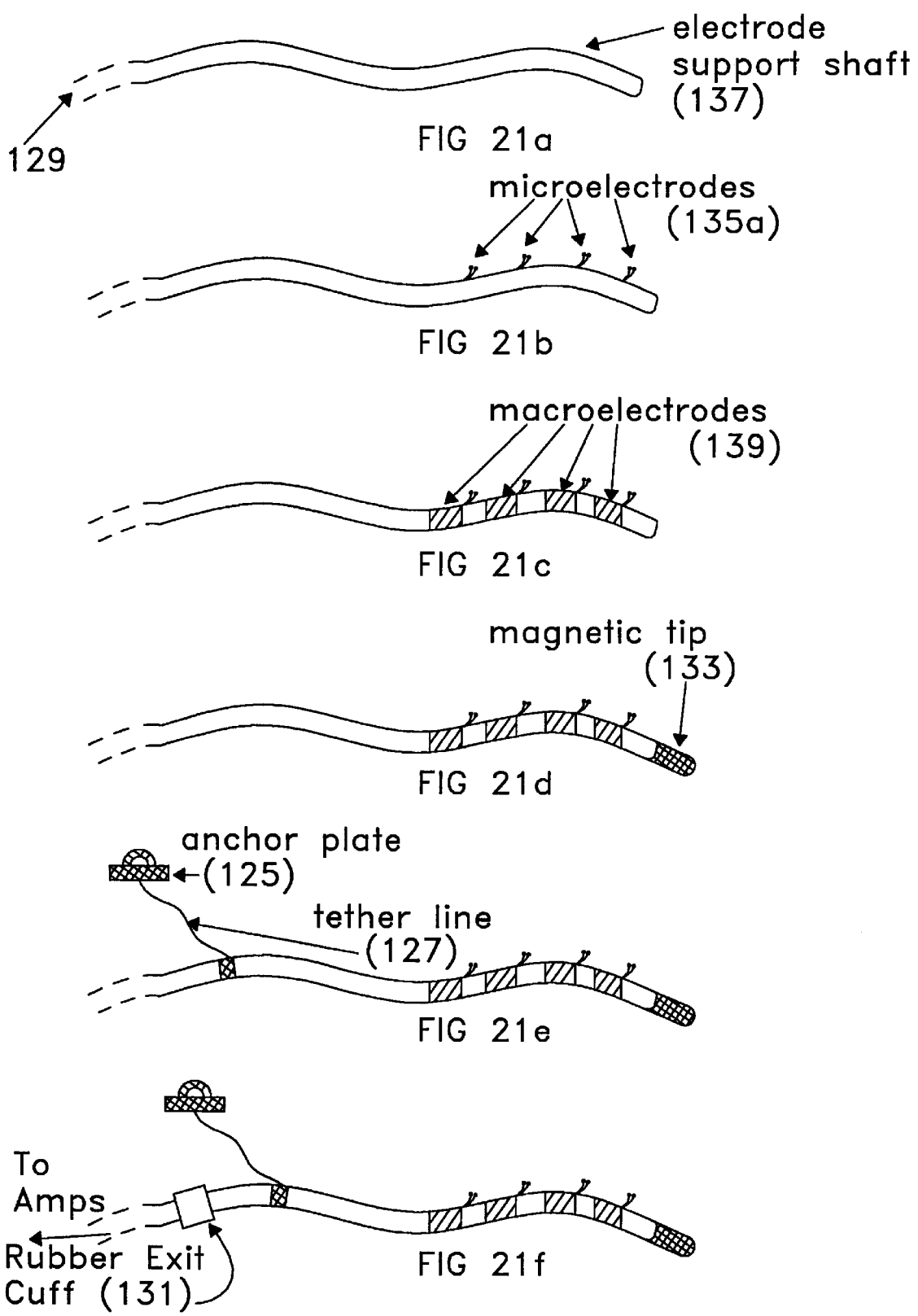
FIG. 21 shows steps in making a dual purpose multicontact electrode assembly useful in performing magnetic stereotactic surgery.

FIG. 21 shows steps in making a dual purpose multicontact electrode assembly useful in performing magnetic stereotactic surgery, wherein there is provided in step a) an electrode support shaft 137 bearing electrical leads 129 for coupling to bipolar microelectrodes 135A and macroelectrodes 139, a plurality of bipolar microelectrodes 135A are attached to electrode support shaft 137 in step b), each of a plurality of macroelectrodes 139 is attached to electrode support shaft 137 adjacent to each of said plurality of bipolar microelectrodes 135A in step c), a magnetic tip 133 is affixed to electrode support shaft 137 in step d), tether line 127 and anchor plate 125 are attached to electrode support shaft 137 at a position on 137 remote from said bipolar microelectrodes 135A and said macroelectrodes 139 in step e), and rubber exit cuff 131 encompasses electrical leads 129 in step f).

Figure 22:
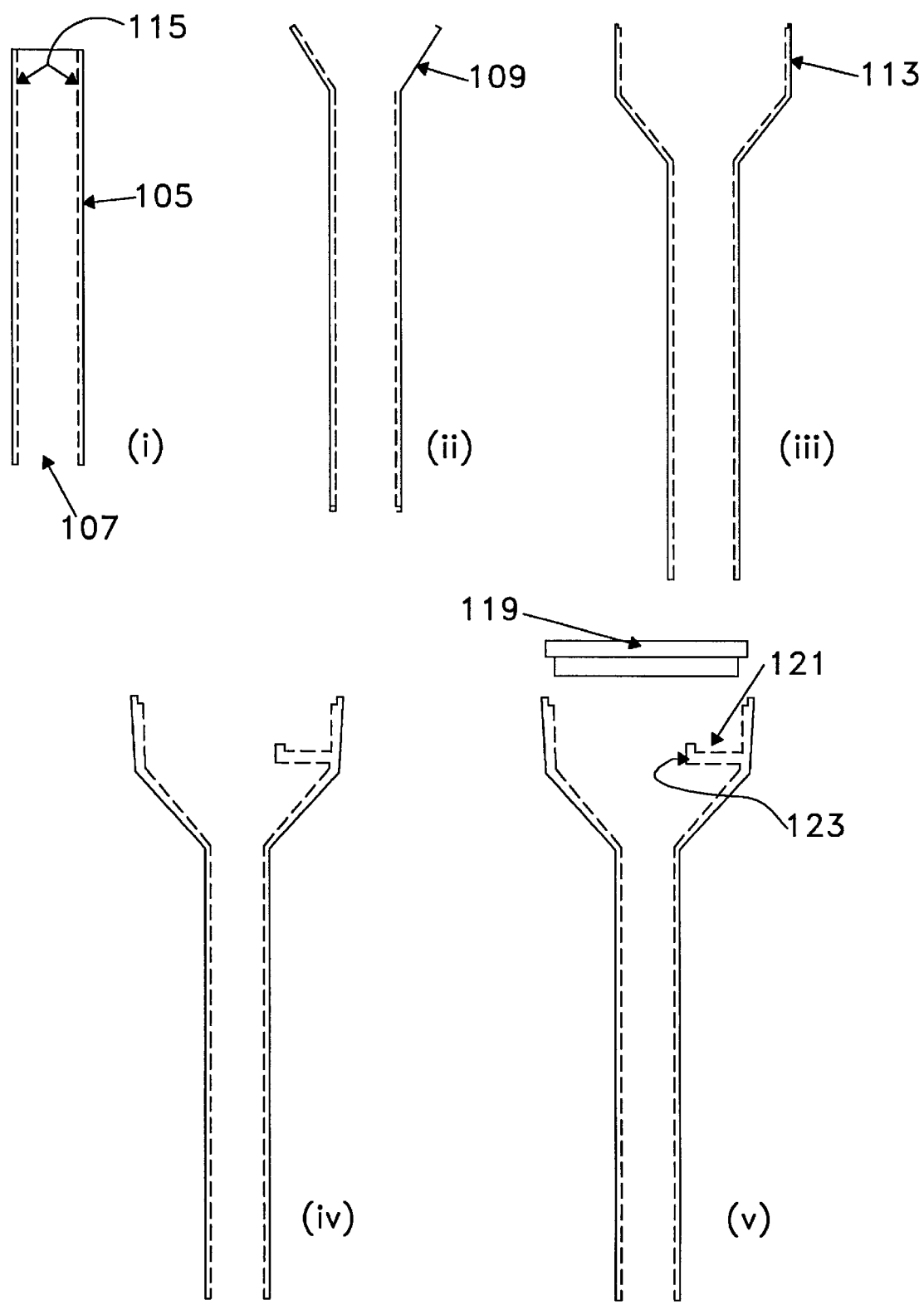
FIG. 22 shows steps in making an introducer tube, according to the invention, for introducing an electrode assembly into a patient.

FIG. 22 shows steps in making introducer tube 101, wherein there is provided an elongate cylinder 105 in step (i), first narrower end of conical neck portion 109 is rigidly attached coaxially to elongate cylinder 105 in step (ii), cylindrical end piece 113 is rigidly attached coaxially to second broader end of conical neck portion 109 in step (iii), docking platform 121 comprising retaining wall 123 is rigidly attached to the inner wall of cylindrical end piece 113 in step (iv), and sealing cap 119 is provided in step (v).

Targeted delivery of therapeutic drugs

One embodiment of a dual purpose stereotactic electrode assembly 103, under the invention, may be used to deliver a measured dose of one or more therapeutic drugs to specific regions of tissues or organs undergoing treatment. In this regard, one or more cells within such regions of tissues, or such regions of tissue themselves, may have been previously monitored for their physiological activity, by means of at least one monitoring electrode 135 mounted on electrode support shaft 137 of electrode assembly 103, prior to drug delivery. Thus, monitoring electrodes 135 on electrode support shaft 137 may be multipolar microelectrodes 135A which are capable of monitoring action potentials from individual cells, or they may be monopolar electrodes 135B capable of recording field potentials from a region of tissue.

The dual purpose cell monitoring/drug delivering electrode assembly embodiment of the invention is particularly useful for delivering a measured dose of a therapeutic drug to a region of previously-monitored tissue within the human brain. Such an electrode assembly 103 may be used, for example, in the treatment of epilepsy by the release of a therapeutic drug to specific regions of the cerebral cortex following monitoring of those regions with monitoring electrodes.

Figure 23:
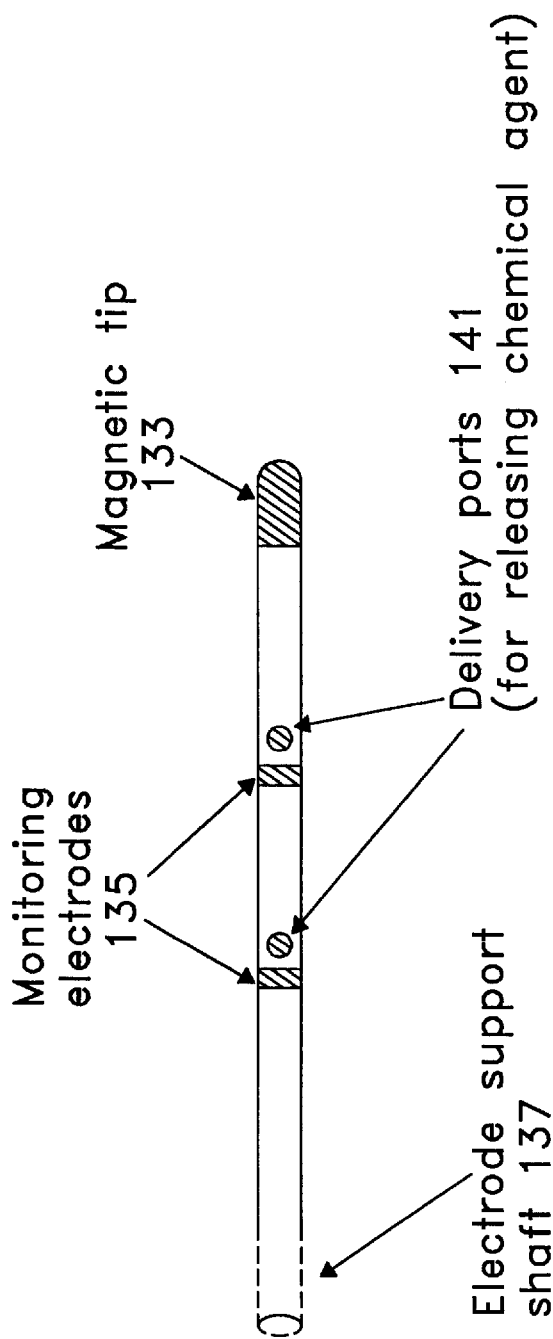
FIG. 23 shows an electrode support shaft of a dual purpose electrode assembly, capable of both monitoring individual neurons and delivering a chemical agent to a specific site within a patient's brain.
Figure 24:
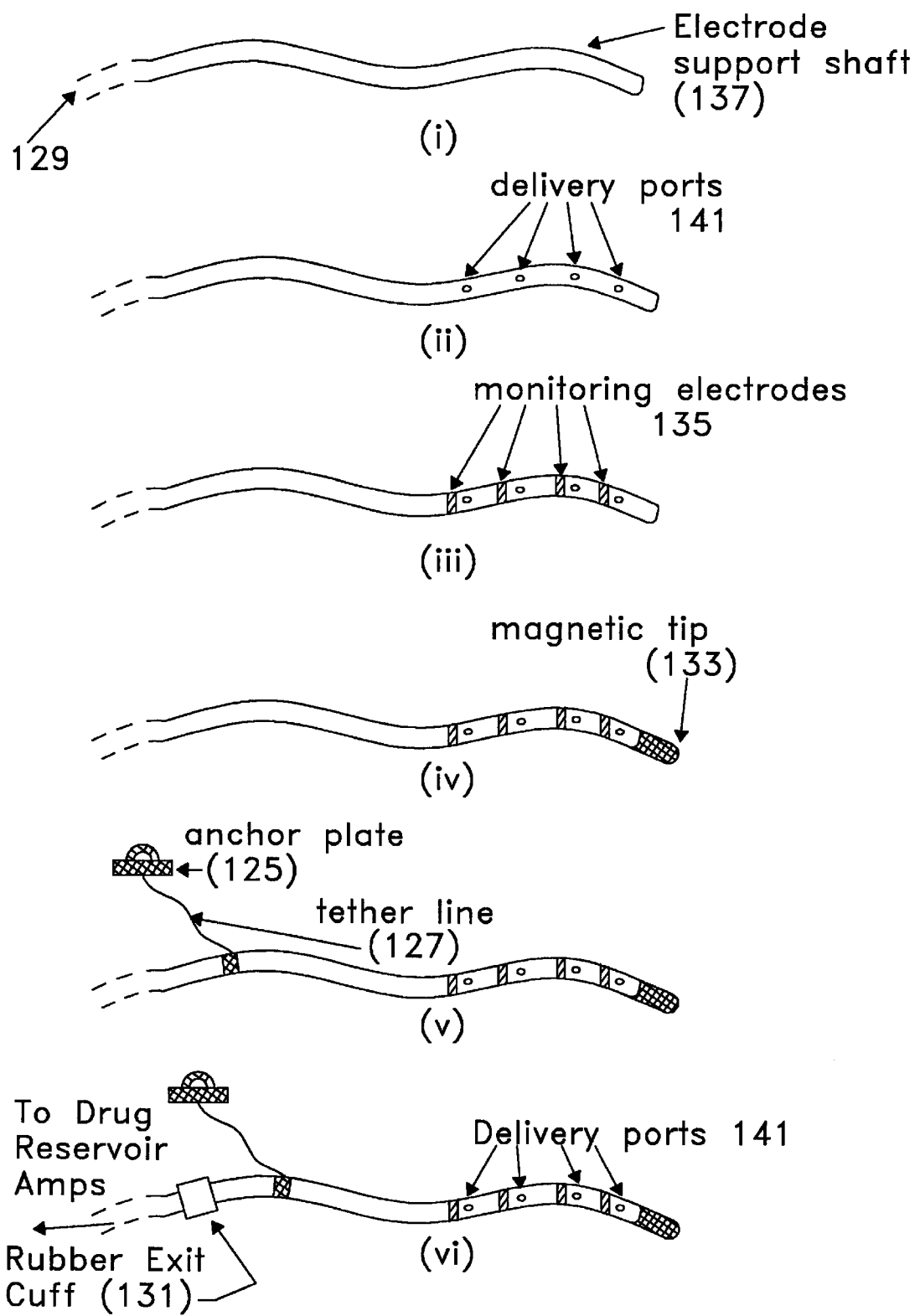
FIG. 24 shows steps in making a dual purpose multicontact electrode assembly capable of both monitoring physiological activity at the individual cell or tissue level, and delivering a chemical agent to a specific site within a patient's tissues.

Referring now to FIG. 23, there is provided a dual purpose electrode support shaft 137 of an electrode assembly 103, bearing a plurality of monitoring electrodes 135 and a plurality of delivery ports 141, which is capable of both monitoring the physiological activity of individual cells or tissues, and delivering a therapeutic drug to a specific site within a patient's tissues. Such an electrode support shaft, and the electrode assembly as a whole, is particularly suited to delivering a therapeutic drug to a specific site within a patient's brain. In one embodiment, such a dual purpose electrode support shaft 137 bears at least one bipolar neuron-monitoring microelectrode 135A capable of monitoring action potentials from individual neurons, and has at least one delivery port 141 capable of releasing a therapeutic drug. In another embodiment, a dual purpose electrode support shaft 137 bears at least one monopolar neuron-monitoring electrode 135B capable of monitoring field potentials from regions of brain tissue, and has at least one delivery port 141 capable of releasing a therapeutic drug. In yet another embodiment, a dual purpose electrode support shaft 137 bears at least one bipolar neuron-monitoring microelectrode 135A capable of monitoring action potentials from individual neurons, and further bears at least one monopolar electrode 135B capable of monitoring field potentials from regions of brain tissue, and has at least one delivery port 141 capable of releasing a therapeutic drug.

The drug-delivering embodiments of the electrode support shaft 137 may be used, under the invention, as an integral part of a flexible, multicontact, dual purpose, magnetically tipped electrode assembly 103, substantially as described above in the context of stereotactic pallidotomy, and may be similarly used in conjunction with introducer tube 101, also described above. The procedures of introducing and positioning electrode support shaft 137 within the target tissue may be performed substantially as described above in the context of magnetic stereotactic surgery, under the invention, and/or according to prior art stereotactic medical procedures. The method of infusing drugs through small openings in the brain catheter would be similar to that described by Lieberbam et al. (Lieberbam et al,.

"Convection-enhanced distribution of large molecules in gray matter during interstitial drug infusion," *J. Neurosurg.*, 82:1021–1029, 1995)

Delivery ports 141 may be positioned along support shaft 137 in a defined spatial relationship with neuron-monitoring electrodes 135A/135B to permit accurate delivery of the drug to the target tissue.

Each drug delivery port 141 may be coupled to at least one drug delivery supply line 145, and each supply line may be connected, through a valve to a suitable mechanism for delivering a liquid. For example, surgical tubing, valves, and pumps known in the art may be used, or adapted for use, in conjunction with the apparatus of the instant invention. A suitable liquid delivering mechanism may in turn be connected to a variable volume reservoir for storing a suitable dose of a therapeutic drug to be delivered during treatment of the target tissue. Drug delivery may then be enacted by the simple expedient of opening the valve and activating a pump, until the reservoir is emptied, or until a suitable measured dose has been released. Each variable volume reservoir and pumping means may be linked to a single delivery port 141, or to a plurality of delivery ports 141. In the latter case, by selectively activating the valve which controls fluid flow to each delivery port 141, the exact site(s) of drug delivery can be controlled.

Figure 25:
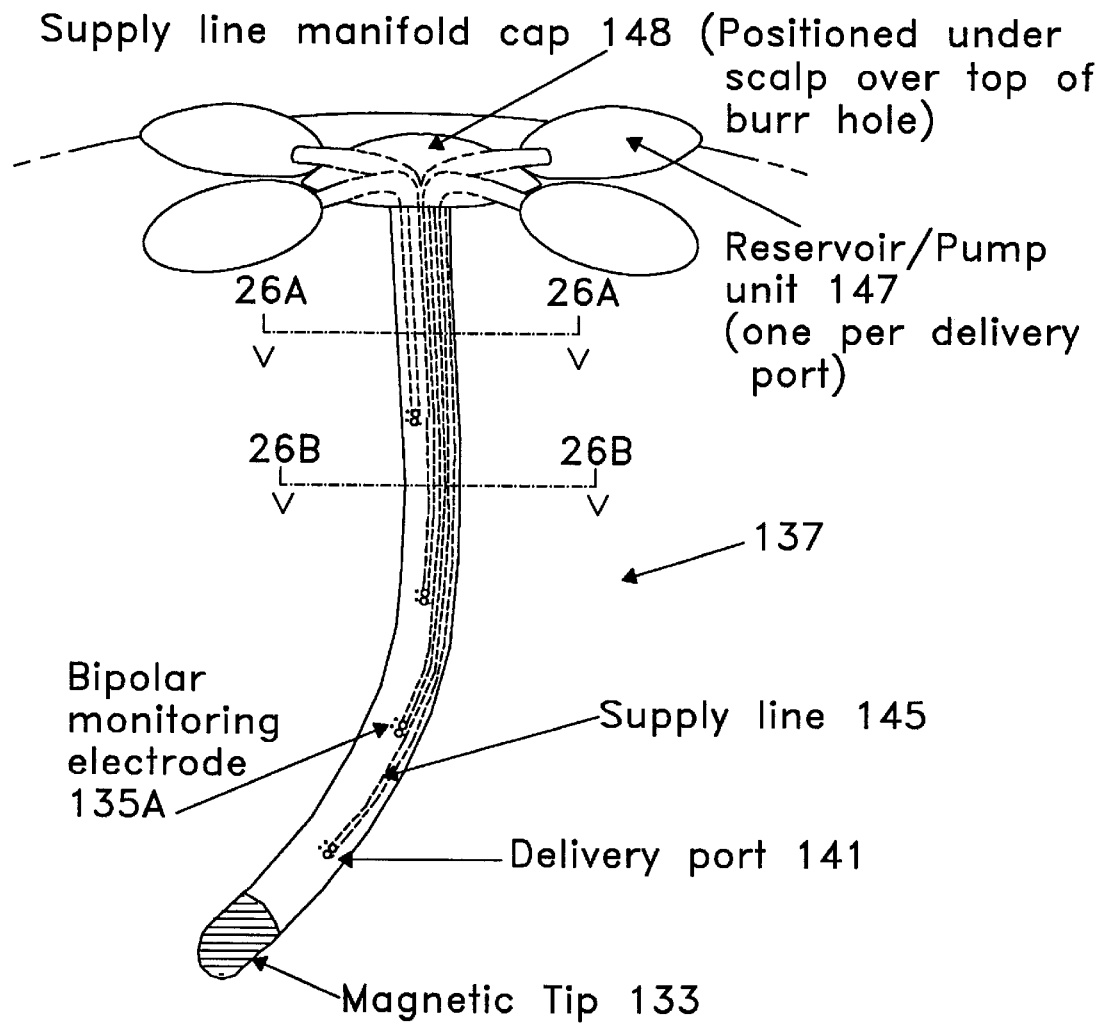
FIG. 25 shows a dual purpose neuron-monitoring/drug delivery electrode assembly, bearing a plurality of multipolar neuron-monitoring electrodes and a plurality of drug delivery ports.
Figure 26A:
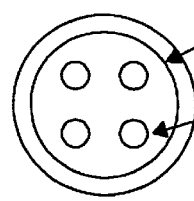
FIGS. 26A and 26B are cross-sectional views of a dual purpose neuron-monitoring/drug delivery electrode assembly at two different positions along its longitudinal axis showing four (26A) and three (26B) drug delivery supply lines, respectively, located within the electrode support shaft.
Figure 26B:
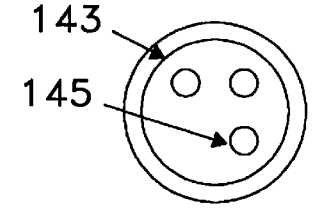

Referring now to FIG. 25 there is shown one embodiment of a dual purpose neuron-monitoring/drug delivery electrode support shaft, bearing a plurality of multipolar neuron-monitoring microelectrodes 135A, and an equal number of spatially paired drug delivery ports 141. Each drug delivery port 141 is connected via a drug delivery supply line 145 to a reservoir/pump unit 147 for storing and dispensing a drug. The plurality of drug delivery supply lines 145 are distributed to the their respective plurality of reservoir/pump units 147 by way of a drug delivery supply line manifold cap 148 located towards the proximal end of electrode assembly 103. The location of a plurality of drug delivery supply lines 145 within the hollow body of the electrode support shaft 137 is shown in FIG. 26A, 26B.

The dual purpose neuron monitoring/drug delivery electrode assembly 103 of the instant invention may be used to administer therapeutic drugs to patients suffering from various disorders of the brain, including both chronic (e.g. epilepsy) and acute (e.g. cerebral aneurysm) conditions. For example, in the case of medically refractory epilepsy, the dual purpose neuron-monitoring/drug delivery electrode assembly 103 comprising a flexible magnetically tipped electrode support shaft 137 may be inserted through a burr hole in the patient's skull via introducer tube 101, such that the magnetic tip 133 of support shaft 137 is approximately in a desired location within the patient's skull. In the magnetic surgery suite, electrode support shaft 137 may be magnetically manipulated under computer control until it occupies the desired position. The location of neuron-monitoring electrodes 135A/135B may be documented in a post-implantation imaging study. Once electrode support shaft 137 is suitably positioned, acute intraoperative monitoring of neurons in contact with electrodes 135A/135B may be undertaken. Alternatively, the patient may be taken from the magnetic surgery suite to the epilepsy monitoring unit, and the physiological activity of a number of neurons may then be monitored chronically, using multipolar microelectrodes 135A, over a period of a number of days. All data generated during this time can be stored using a multichannel tape recorder (Racal, Herndon, Va.), and may be analyzed off-line in the laboratory. Based on the data thus obtained and on criteria of physiologically normal parameters, an informed decision can be made as to whether drug treatment is indicated, and if so, the optimum treatment regime (nature of the drug, dosage, etc.) to be followed. Subsequently an appropriate dose of one or more therapeutic drugs may be selectively released from one or more drug delivery ports 141 positioned on electrode support shaft 137.

The functional consequences of drug treatment may be assessed either in the epilepsy monitoring unit prior to removal of the dual purpose electrode assembly 103, or subsequently. If, after assessing the patient, further treatment is indicated, either an additional dose of the same drug, or a first dose of a different drug, may be administered to those neurons that have already been monitored. Further, if patient assessment in the epilepsy monitoring unit indicates that it is desirable to monitor, and potentially administer a therapeutic drug to, additional neurons located at a different site of the cerebral cortex, electrode assembly 103 may be retracted into introducer tube 101, and the patient returned to the magnetic surgery suite. The above process may be repeated until a satisfactory result is achieved. A method for targeted delivery of therapeutic drugs to a patient, according to one embodiment of the invention, is described in Example 2.

As will be readily apparent to the skilled artisan, epilepsy treatment may also be performed by the selective inactivation of previously monitored neurons or regions of brain tissue, substantially according to the methods and apparatus, under the invention, described herein in the context of stereotactic pallidotomy. As discussed above, neuron inactivation may be effected by various treatments, including irradiation, treatment with a toxic chemical, cryogenic treatment and chronic electrical stimulation.

EXAMPLE 1

METHOD OF PERFORMING MAGNETIC STEREOTACTIC PALLIDOTOMY

Introducer tube 101 is stereotactically inserted through a burr hole in the patient's skull such that the open distal end 107 of introducer tube 101 is positioned close to the lateral globus pallidus. A dual purpose multicontact electrode assembly 103 comprising a flexible electrode support shaft 137 having a magnetic tip 133 is inserted into introducer tube 101, such that magnetic tip 133 of support shaft 137 is approximately in a desired location within the patient's brain. The patient is brought to the magnetic surgery suite, and electrode support shaft 137 of electrode assembly 103 is magnetically pulled into the globus pallidus, generally along the long axis of the globus pallidus, along a preselected trajectory. Once electrode support shaft 137 is suitably positioned to occupy the desired volume within the globus pallidus, the patient is removed from the magnetic surgery suite and returned to the hospital ward. While on the ward, the physiological activity of a number of globus pallidus neurons is monitored using bipolar microelectrodes 135A. Based on the recordings of physiological activity thus obtained and on criteria of physiologically normal parameters, radio frequency lesions are made at the site of those neurons targeted for inactivation, by energizing the appropriate macroelectrode(s) 139 with a lesion-producing electric current. The functional consequences of the newly-formed lesions are assessed on the ward by testing the patient prior to removal of electrode assembly 103 from the patient. If the results are satisfactory, the electrode assembly is removed. If it is desirable to monitor, and potentially lesion, additional neurons located within a different volume of the globus pallidus, electrode assembly 103 is retracted into introducer tube 101. The patient is returned to the magnetic surgery suite, and the process is repeated until a satisfactory result is achieved.

EXAMPLE 2

TARGETED DRUG DELIVERY FROM A DUAL PURPOSE ELECTRODE ASSEMBLY FOR THE TREATMENT OF EPILEPSY

Introducer tube 101 is stereotactically inserted through a burr hole in the patient's skull such that the open distal end 107 of introducer tube 101 is positioned within the cerebral cortex. A dual purpose neuron-monitoring/drug delivery electrode assembly 103 comprising a flexible electrode support shaft 137 having a magnetic tip 133 is inserted into introducer tube 101, such that the magnetic tip 133 of support shaft 137 is approximately in a desired location within the patient's skull. The patient is brought to the magnetic surgery suite, and electrode support shaft 137 of electrode assembly 103 is magnetically manipulated until it occupies the desired position. Once electrode support shaft 137 is suitably positioned, the patient is removed from the magnetic surgery suite and taken to the epilepsy monitoring unit, where the physiological activity of a number of neurons is monitored. Based on the recordings of physiological activity thus obtained and on criteria of physiologically normal parameters, a suitable dose of one or more therapeutic drugs is released from one or more selected drug delivery ports 141.

The functional consequences of drug treatment is assessed in the epilepsy monitoring unit by testing the patient prior to removal of dual purpose electrode assembly 103. If the results are satisfactory, electrode assembly 103 is removed from the patient. If it is desirable to monitor, and potentially administer a therapeutic drug to, one or more different regions of the cerebral cortex, electrode assembly 103 is retracted into introducer tube 101. The patient is then returned to the magnetic surgery suite, and the process is repeated until a satisfactory result is achieved.

Although the instant invention has been described herein principally within the context of performing stereotactic pallidotomy, as will be apparent to the skilled artisan, the apparatus of the instant invention is particularly suited to performing surgery on the brain, in general, and may be used effectively for performing other medical procedures, including but not limited to, thalamotomy, controlled lesioning to treat epilepsy, and targeted delivery of therapeutic drugs.

The Risk Benefit Ratio i. Neural prosthesis risk/benefit

The clinical usefulness of an auditory neural prosthetic device depends on several variables, most importantly the risk-benefit ratio for a given device. An ideal device effectively restores hearing without risk to the patient's overall health. Salient features of two types of devices are outlined below.

Since primary auditory cortex 150 is situated in temporal lobe 156, neurosurgeons expose this portion of the brain routinely during a wide range of operations. In the non-dominant temporal lobe, unlike the brainstem, the auditory region is not surrounded by vital structures. If a patient is diagnosed with an infiltrating tumor of the non-dominant auditory cortex, for example, the neurosurgeon can resect this tissue with very little risk of complication.

Another example is temporal lobe surgery for intractable epilepsy. Most patients who undergo this surgery are in good general health but suffer from seizures periodically. Usually, chronic epilepsy is not a life threatening condition, and many patients have seizures for decades during which time they are able to work and raise families.

Since most forms of epilepsy are medically "tolerable," surgical treatment directed at curing epilepsy is only justified when it is highly effective and carries with it very low risk of morbidity and mortality. A properly selected patient in good general health has less than a one percent chance of developing a significant neurologic complication following an elective non-dominant temporal lobectomy for intractable epilepsy, and a 70 percent chance of being cured of their seizures. In that setting, the risk/benefit ratio is strongly in the patient's favor. An operation designed exclusively to place a stimulating neural prosthetic electrode onto non-dominant auditory cortex could be carried out under local anesthesia and take less than two hours operating time. This procedure would entail even less medical risk than a standard epilepsy resection.

ii. Magnetic pallidotomy risk/benefit

Compared with prior art stereotactic pallidotomy, magnetic pallidotomy according to the instant invention has, in theory, less risk and greater benefit to the patient, for the following reasons. Because of the ability of the electrode support shaft to be directed to occupy a specific conformation within the target tissue and the presence of a plurality of neuron-monitoring microelectrodes, a target volume of the globus pallidus can be accesses, and neurons from a number of sites within that target volume can be monitored with a single pass through the brain. In contrast, neuron-monitoring electrodes of the prior art would need to be passed through the brain a number of times to access an equivalent volume of target tissue.

Secondly, by combining the functions of neuron-monitoring and lesion-production in a single dual purpose electrode assembly, according to the invention, the need for replacing a neuron-monitoring electrode support with a lesion-producing electrode support is eliminated, and consequently the risk of error in electrode support misplacement is also eliminated.

Furthermore, the safety and efficacy of pallidotomy is strongly influenced by the ability to effectively monitor and assess brain tissue being considered for inactivation. The ability to monitor a number of neurons over an extended period of time, on the ward, allows for the gathering of more precise information on the physiologic status of each neuron, and a more informed decision to be made on which regions of the tissue are to be targeted for lesion production.

What is claimed is:

1. A neurological apparatus comprising:

an electrode support shaft;

at least one bipolar neuron-monitoring microelectrode arranged along said electrode support shaft; and at least one lesion-producing macroelectrode arranged along said electrode support shaft, wherein said electrode support shaft comprises a flexible outer sheath, each of said at least one bipolar neuron-monitoring microelectrodes comprises a pair of electrical contacts, said pair of electrical contacts closely juxtaposed, each of said bipolar neuron-monitoring microelectrodes lying external to said flexible outer sheath of said electrode support shaft, wherein each of said pair of electrical contacts is constructed to monitor electrical activity produced by between one and ten neurons, and wherein each pair of electrical contacts is configured to be coupled to a differential amplifier, said differential amplifier capable of outputting signals and monitoring the activity of at least one neuron.

2. An apparatus for performing pallidotomy on a patient's brain, comprising:

a) an electrode support shaft having a distal tip;

b) an introducing means for introducing said electrode support shaft into the patient's brain, said electrode support shaft housed within said introducing means;

c) a separately monitoring means, on said electrode support shaft, for monitoring the physiological activity of individual neurons;

d) an inactivating means, on said electrode support shaft, capable of inactivating neurons; and e) a retrieving means attached to said electrode support shaft for retrieving said electrode support shaft from the patient's brain into said introducing means.

3. The apparatus according to claim 2, wherein said electrode support shaft bears a magnet fixedly attached to the distal tip of said electrode support shaft, wherein said magnet is responsive to an applied external magnetic field, and wherein said introducing means comprises an introducer tube, and said retrieving means comprises a tether line.

4. The apparatus according to claim 38, wherein said monitoring means comprises at least one bipolar neuron-monitoring microelectrode, said inactivating means is selected from the group consisting of a lesion-producing macroelectrode, a cryogenic device, a neuron-stimulating electrode, and a means for delivering a chemical agent.

5. The apparatus according to claim 4, wherein said inactivating means comprises at least one lesion-producing macroelectrode capable of emitting radio frequency energy.

6. A neurological apparatus, comprising an introducer tube having a proximal end and a distal end and an electrode assembly, wherein said introducer tube comprises:
an elongate cylindrical portion;
a conical neck portion continuous with said elongate cylindrical portion, wherein said conical neck portion increases in diameter in a direction away from said elongate cylindrical portion;
a short cylindrical end piece continuous with said conical neck portion; and
means for sealing the proximal end of said introducer tube; and wherein said electrode assembly comprises:
a flexible electrode support shaft having a distal portion and a distal tip;
a magnet located at the distal tip of said flexible electrode support shaft, said magnet responsive to an applied magnetic field;
at least one neuron-inactivating macroelectrode positioned on the distal portion of said flexible electrode support shaft;
at least one neuron-monitoring microelectrode disposed on the distal portion of said flexible electrode support shaft; and
a tether line attached to said flexible electrode support shaft at a location remote from said at least one neuron-monitoring microelectrode.

7. The apparatus according to claim 6, wherein each of said at least one neuron-monitoring microelectrode is spatially paired with each of said at least one neuron-inactivating macroelectrode.

8. The apparatus according to claim 6, wherein each of said at least one neuron-monitoring microelectrodes is multi-polar.

9. The apparatus according to claim 6, wherein each of said at least one neuron-monitoring microelectrode is bipolar and comprises a pair of juxtaposed electrical contacts.

10. The apparatus according to claim 6, wherein said at least one neuron-monitoring microelectrode monitors neuronal activity, and said neuronal activity is used to determine whether to energize said at least one neuron-inactivating macroelectrode.

11. An apparatus for producing at least one lesion in a globus pallidus of a human brain, comprising:
a flexible electrode support shaft having a magnetic tip responsive to an applied external magnetic field, wherein said flexible electrode support shaft is configured to be positioned along the globus pallidus in response to application of said external magnetic field;
a plurality of lesion-producing macroelectrodes arranged along said flexible electrode support shaft; and
a plurality of neuron-monitoring microelectrodes arranged along said flexible electrode support shaft, said plurality of neuron-monitoring microelectrodes for outputting neuron activity signals, and wherein selected lesion-producing macroelectrodes are energized, in accordance with said neuron activity signals outputted, to produce said at least one lesion in the globus pallidus.

12. The apparatus according to claim 1, wherein each of said plurality of neuron-monitoring microelectrodes is bipolar and has a defined spatial orientation on said flexible electrode support shaft relative to said plurality of lesion-producing macroelectrodes.

13. The apparatus according to claim 1, wherein each of said plurality of neuron-monitoring microelectrodes comprises a pair of juxtaposed electrical contacts and each of said plurality of neuron-monitoring microelectrodes is arranged on said flexible electrode support shaft coincidental with, and external to, each of said plurality of lesion-producing macroelectrodes.

14. An apparatus for making one or more lesions in a brain, comprising:
a flexible support shaft having a magnetic tip responsive to an external magnetic field, wherein said flexible support shaft can be precisely moved by application of an external magnetic field;
a plurality of neuron-monitoring microelectrodes arranged along said flexible support shaft wherein each of the neuron-monitoring microelectrodes is constructed to sense electrical activity produced by between one and ten neurons;
at least one lesion-producing macroelectrode disposed on said flexible support shaft; and
a fluid-coated introducer tube for introducing said flexible support shaft into the brain, thereby allowing said at least one lesion-producing macroelectrode to make said one or more lesions in the brain.

15. The apparatus of claim 14, wherein said at least one lesion-producing macroelectrode comprises a plurality of lesion-producing macroelectrodes arranged along said flexible support shaft.

16. The apparatus of claim 15, wherein said plurality of lesion-producing macroelectrodes are capable of emitting radio frequency energy.

17. A neurological apparatus, comprising:
a flexible electrode assembly including an electrode support shaft, said electrode support shaft having a magnetic tip which is responsive to the presence of an external magnetic field;
one or more lesion-producing macroelectrodes arranged along said electrode support shaft;
an introducer tube for introducing said electrode support shaft into a brain such that said magnetic tip is approximately in a desired location within the brain; and a plurality of neuron-monitoring microelectrodes arranged along said electrode support shaft, wherein each neuron-monitoring microelectrode is constructed to sense the electrical activity produced by between one and ten neurons, and wherein said electrode support shaft is movable within the brain by application of an external magnetic field.

18. The apparatus according to claim 17, wherein said one or more lesion-producing macroelectrodes is spatially paired with one of said plurality of neuron-monitoring microelectrodes arranged along said electrode support shaft, and each of said plurality of lesion-producing macroelectrodes is capable of inactivating one or more neurons by emitting radio frequency energy.

19. A neurological apparatus comprising:

an electrode support shaft having a magnetic tip;

at least one monopolar or multipolar neuron-monitoring microelectrode arranged along said electrode support shaft each microelectrode being configured to monitor the electrical activity of between one and ten neurons; and at least one lesion-producing macroelectrode arranged along said electrode support shaft.

20. The apparatus of claim 19, wherein said electrode support shaft comprises a flexible sheath.

21. A neurological apparatus comprising:

a support shaft;

at least one monopolar neuron-monitoring microelectrode arranged along said support shaft each microelectrode being configured to monitor the electrical activity of between one and ten neurons; and at least one lesion-producing macroelectrode arranged along said support shaft.

* * * * *